United States Patent
Osorio et al.

(10) Patent No.: US 7,346,391 B1
(45) Date of Patent: Mar. 18, 2008

(54) CEREBRAL OR ORGAN INTERFACE SYSTEM

(75) Inventors: Ivan Osorio, Leawood, KS (US); Mark G. Frei, Lawrence, KS (US)

(73) Assignee: Flint Hills Scientific LLC, Lawrence, KS (US)

( * ) Notice: Subject to any disclaimer, the term of this patent is extended or adjusted under 35 U.S.C. 154(b) by 605 days.

(21) Appl. No.: 10/940,289

(22) Filed: Sep. 14, 2004

Related U.S. Application Data

(63) Continuation-in-part of application No. 10/430,133, filed on May 5, 2003, now Pat. No. 7,177,678, which is a continuation of application No. 09/416,471, filed on Oct. 12, 1999, now Pat. No. 6,560,486.

(51) Int. Cl.
*A61N 1/375* (2006.01)

(52) U.S. Cl. ............................ 607/2; 607/36; 607/139; 600/378

(58) Field of Classification Search .................. 607/2, 607/45, 139, 36, 3, 60; 600/378, 544
See application file for complete search history.

(56) References Cited

U.S. PATENT DOCUMENTS

| | | | |
|---|---|---|---|
| 4,127,110 A | 11/1978 | Bullara | |
| 4,146,029 A * | 3/1979 | Ellinwood, Jr. | ........... 604/891.1 |
| 4,186,749 A | 2/1980 | Fryer | |
| 4,373,527 A * | 2/1983 | Fischell | ..................... 604/891.1 |
| 4,471,786 A | 9/1984 | Inagaki et al. | |
| 5,159,927 A | 11/1992 | Schmid | |
| 5,220,929 A | 6/1993 | Marquit | |
| 5,480,416 A | 1/1996 | Garcia et al. | |
| 5,549,620 A | 8/1996 | Bremer | |
| 5,928,272 A | 7/1999 | Adkins et al. | |
| 6,016,449 A | 1/2000 | Fischell et al. | |
| 6,096,019 A * | 8/2000 | Andrews | ..................... 604/500 |
| 6,113,553 A | 9/2000 | Chubbuck | |
| 6,134,474 A | 10/2000 | Fischell et al. | |
| 6,185,455 B1 | 2/2001 | Loeb et al. | |
| 6,560,486 B1 * | 5/2003 | Osorio et al. | .................. 607/45 |
| 6,749,581 B2 * | 6/2004 | Thompson et al. | ........... 604/48 |
| 6,961,619 B2 * | 11/2005 | Casey | ......................... 607/61 |
| 7,177,678 B1 * | 2/2007 | Osorio et al. | .................. 607/2 |

* cited by examiner

*Primary Examiner*—Kennedy J. Schaetzle
(74) *Attorney, Agent, or Firm*—Donald R. Schoonover

(57) ABSTRACT

A cerebral and/or interface system has a housing mechanism configured to be at least partially spaced in a cavity formed in the subject's skull; an attaching mechanism for attaching the housing mechanism to the subject's skull; a sealing mechanism for providing a fluid-tight seal between the housing mechanism and the subject's skull; a control mechanism spaced within the housing mechanism; a communication mechanism with one or more sensors embedded in the subject's brain connecting the control mechanism to the subject's brain; and a power source spaced within the housing mechanism. Optional embodiments include a treatment portion for cooling or heating adjacent tissue, a medicament portion for administering medicament to adjacent tissue, a separate auxiliary compartment with a removable lid secured to or spaced apart from the housing mechanism, contacts extending outwardly from housing mechanism, and/or a supporting mechanism for precisely displacing the housing mechanism angularly or along x-, y-, and z-axes.

3 Claims, 16 Drawing Sheets

Fig. 14A
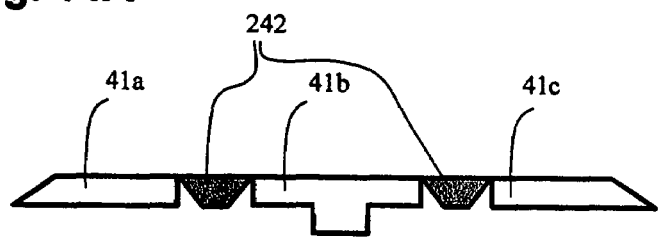
Fig. 14B
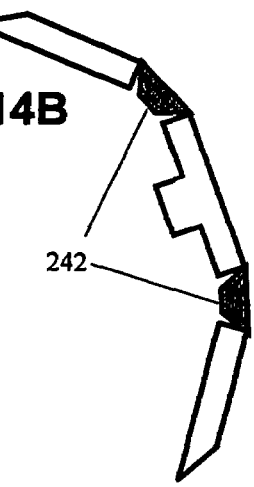
Fig. 14C
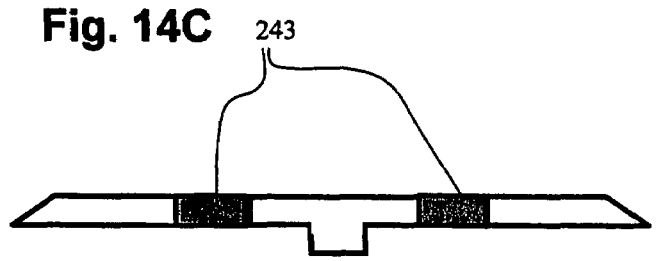
Fig. 14D
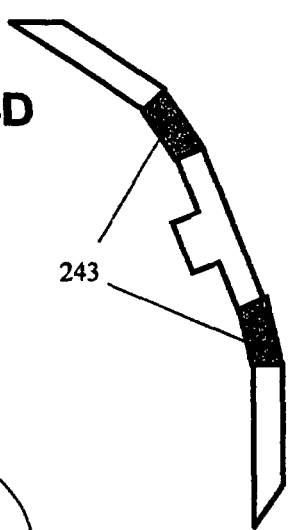
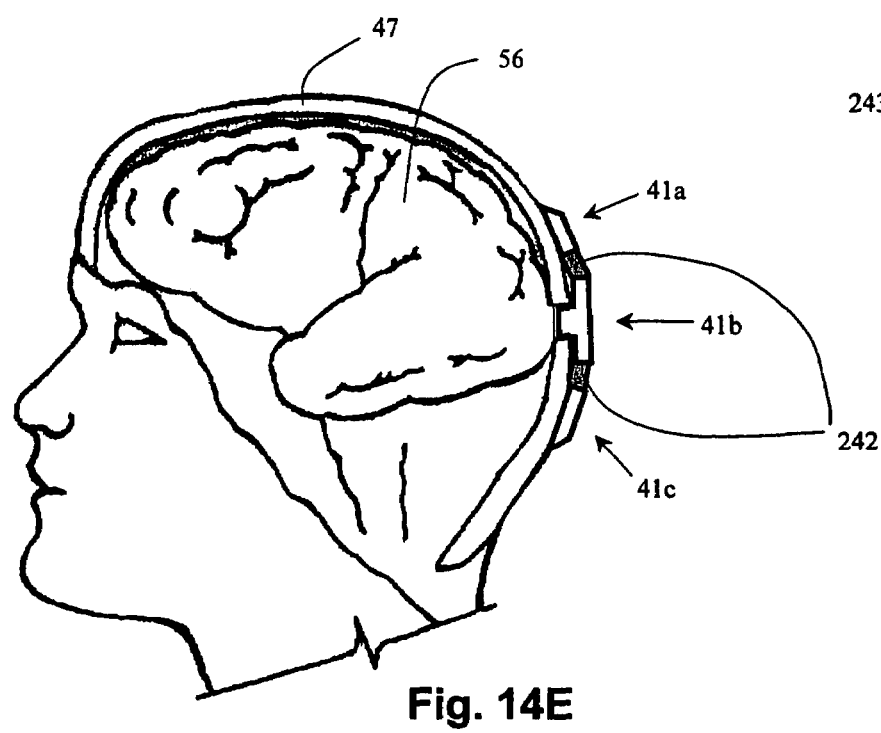
Fig. 14E

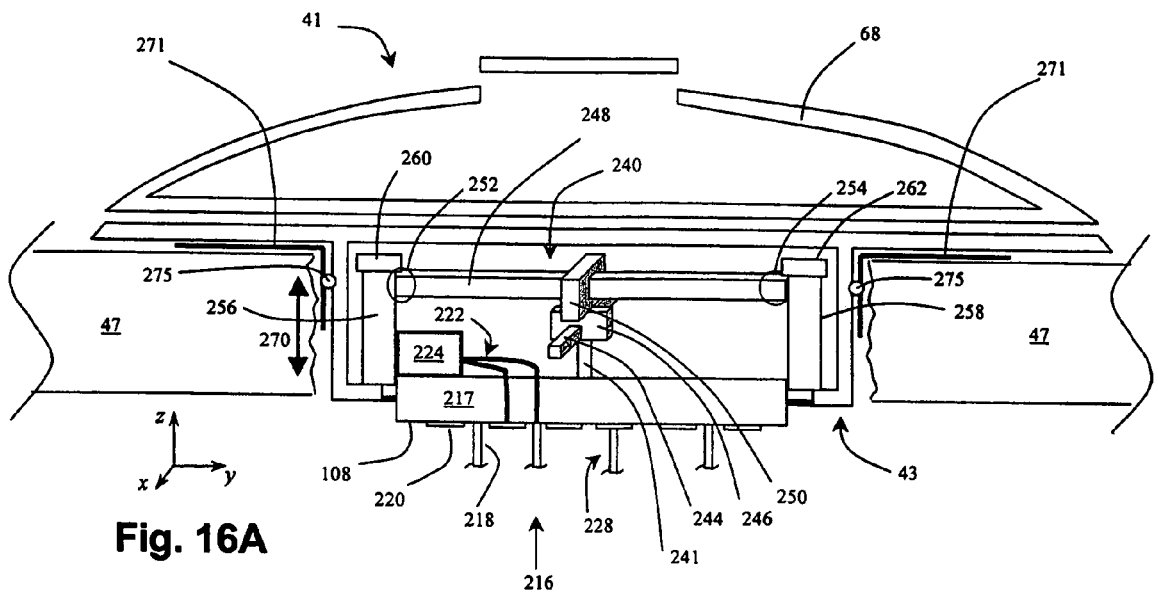
Fig. 16A
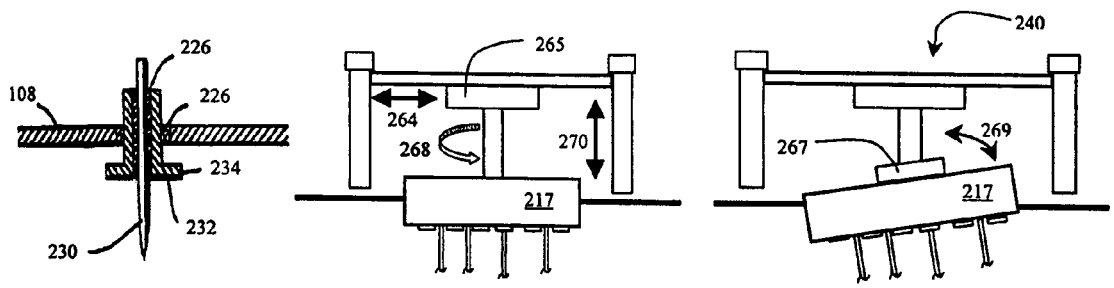
Fig. 16B  Fig. 16C  Fig. 16D
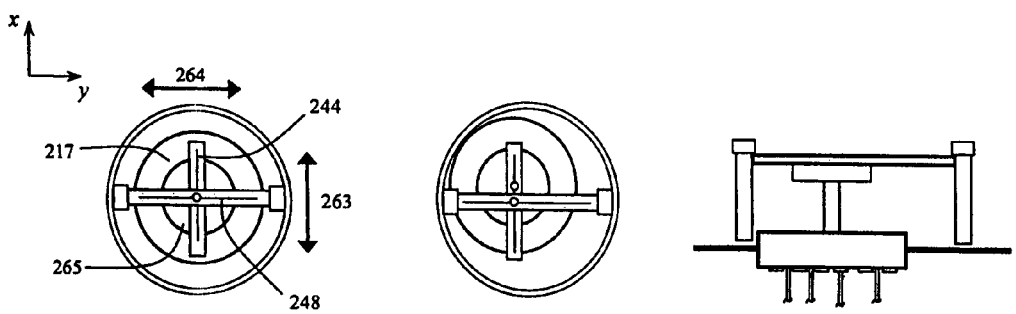
Fig. 16E  Fig. 16F  Fig. 16G

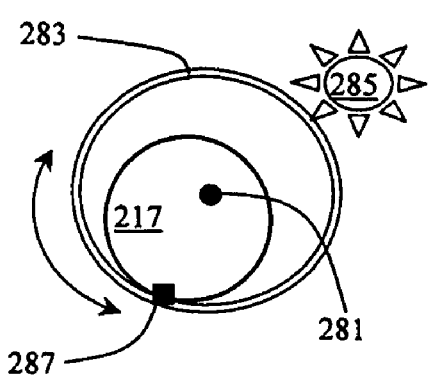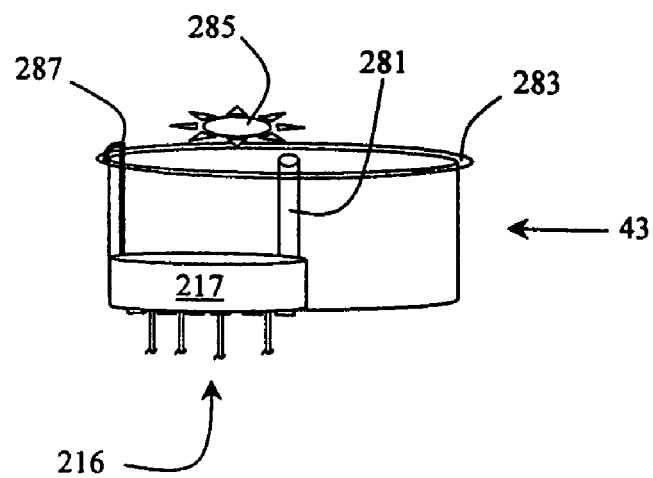
Fig. 16 H              Fig. 16 I

CEREBRAL OR ORGAN INTERFACE SYSTEM

CROSS REFERENCE TO RELATED APPLICATIONS

This application is a continuation-in-part of U.S. application Ser. No. 10/430,133 filed May 5, 2003, now U.S. Pat. No. 7,177,678 which is a continuation of application Ser. No. 09/416,471 filed Oct. 12, 1999, now U.S. Pat. No. 6,560,486.

BACKGROUND OF THE INVENTION

1. Field of the Invention

The present invention relates to the field of neuroscience and, more particularly without limitation, to a subfield of neuroprostheses for housing devices spaced in close proximity to organs such as the brain, which will be the focus of this disclosure. However, those skilled in the art will appreciate that this invention may be applied to any organ in close proximity to body structures, such as bones, which can harbor and support devices within their confines.

2. Glossary of Terms and Useful Definitions

The term "electroencephalogram" ("EEG") refers to voltage potentials recorded from the scalp and encompasses any recordings obtained from a source outside the dura mater. The term "electrocorticogram" ("ECoG") refers to voltage potentials recorded intracranially, e.g., with sensors placed within the skull, epidurally, subdurally, or intracortically/cerebrally. "EKG" is an abbreviation for the term "electrocardiogram," "EMG" for the term "electromyogram" which records electrical muscle activity, and "EOG" for the term "electrooculogram" which records eye movements.

The term "real-time" as used herein describes a system with negligible latency between input and output.

As used herein, the term "outer table" refers to the outer bony sheet of the skull in contact with the scalp; the term "inner table" refers to the inner bony sheet of the skull in contact with the outermost brain membrane or "dura"; and the term "diploe" refers to the part of the skull between the outer table and inner table that provides nutrients and minerals necessary for developing and maintaining the skull.

3. Description of the Related Art

Humans and animals have several normal states of behavior, such as wakefulness and sleep, as well as multiple sub-states, such as attentive wakefulness and REM sleep. Abnormal states of behavior in humans and animals include reversible states, such as seizures, and progressive irreversible states, such as dementia.

Recent advances in the field of clinical neurosciences have opened a new era for the use of and need for implantable therapeutic devices. For example, the use of prostheses, for the diagnosis or treatment of neurologic illnesses, is rapidly growing and will continue to expand as new applications are found. As new technological developments take place, so does the opportunity to improve current designs or performance, decrease power requirements or cost, and/or minimize complications associated with chronic implantation. For instance, a device to electrically stimulate brain regions, via chronically implanted electrodes for Parkinson's disease, has been recently approved for commercial use by the Food and Drug Administration. Implantable devices to detect and control abnormal brain states, such as epileptic seizures, are currently under development.

Currently, brain devices, such as the one used for Parkinson's disease, are implanted under the collarbones at a substantial distance from the brain. For example, the use of wires or conductors to carry a signal into or out of the brain, requires a special, time consuming procedure and careful placement of wires and connectors to avoid scalp/skin erosion, a common and serious complication which often requires removal of the device with loss of benefit to the subject. More specifically, such an approach has several significant disadvantages: (i) the long conductors for connecting the device to electrodes implanted in the brain require tunneling under the scalp and skin, thereby requiring prolonged surgery and anesthesia for installation; (ii) the tract along the conductors often becomes infected requiring, in many cases, that the conductors be explanted with consequent cessation of treatment to the subject; (iii) the conductors often erode the overlying scalp, forcing removal of the cables so that healing can take place but, at the same time, removing the means for warning of or treating impending abnormal activities; (iv) the conductors often fracture since they are subjected to torsional and other forces generated by normal head/neck movements with consequent corrective surgery to replace the faulty conductors; (v) the distance and time for delivery of therapy to a target can be substantially longer, potentially decreasing efficacy due to the delay between onset of change of state and arrival of therapy at the target; and (vi) in the case of telemetered signals, closer proximity of the emitter to the receiver would increase fidelity of the transmitted signals and decrease power requirements, hence prolonging battery life and decreasing frequency of surgical replacement procedures.

The placement of prior art brain devices outside the skull, such as in the infra-clavicular regions, is due to lack of space between the brain and the skull to position such devices and also to the inability to recognize the potential to convert virtual into real spaces without affecting the integrity of the skull. Indeed, while the brain is closely apposed to the inner table of the skull, leaving no usable space to safely house devices of certain size, the skull has several properties that enable conversion of virtual into real space for use in the integrated and ergonomic placement of devices. These properties, which heretofore have not been fully exploited, include:

(a) sufficient wall thickness to allow a housing to access systems/electronic components partially or completely within the confines of the two tables of the skull;

(b) high tensile strength to safely support said devices; and (c) semi-circular configuration allowing uniform distribution of forces over its surface.

In addition, scalp tissue has the elasticity or deformability necessary for accommodation of housing mechanisms which may protrude outside the outer table.

Accurate and reproducible real-time detection or prediction of behavioral or biological signal changes associated with abnormal brain activities has not been generally possible as such events typically occur unpredictably. This limitation has been recently overcome, making it possible to accurately detect various types of brain state changes, such as the onset of epileptic seizures, etc., as taught, for example, in U.S. Pat. No. 5,995,868, issued Nov. 30, 1999 to Ivan Osorio et al.

Thus, what is needed is an interface system that permits spacing essential mechanisms which perform these and/or other tasks in close proximity to a subject's brain or other organ.

SUMMARY OF THE INVENTION

The present invention includes improvements for enabling the ergonomic, economic, safe, and effective placement of devices strategically in reference to the brain and/or other body organ(s) of a human or animal subject, thereby creating an interface between the brain/organs and the user to sense, monitor, quantify, or analyze the brain activity of the subject; to predict or detect changes in such brain activity; to allow warning, logging, recording, or storing data; and to allow prevention and/or control of undesirable changes in such brain activity, such as the activity changes associated with an epileptic seizure, for example.

The interface system of the present invention includes: at least one housing mechanism configured to be spaced at least in part in a cavity formed in the subject's skull; an attaching mechanism configured to attach the housing mechanism to the subject's skull; a sealing mechanism configured to provide a fluid-tight seal between the housing mechanism or parts thereof and the subject's skull; and a communication mechanism configured to allow uni-directional or bi-directional communication between the housing mechanism or devices associated therewith and the brain or other organs. The communication is termed uni-directional when devices are only used for sensing or only used for open-loop control/output, and bi-directional if devices obtain signals from the brain or other organs and produce an output to the brain/body. Examples of uni-directional operation of the communication mechanism include but are not limited to: (1) a system that comprises one or more sensors implanted in the subject's brain or other organ(s) and connected, e.g., via conductors to one or more devices spaced inside the housing, to receive signals from the sensors and then, condition, analyze, and/or store those signals; and (2) an "open loop" controller that delivers electrical stimulation or other forms of therapy to the brain (without basing when to stimulate the brain on information acquired from the brain) through connected electrodes without receiving or processing brain signals. Examples of bidirectional communication include but are not limited to: receiving signals from a sensor, detecting a change of brain and/or body state, and then activating an output mechanism in response thereto to control the state of the system.

Some examples of devices that may be placed within or in relation or reference to the housing mechanism include a sensing/conditioning mechanism, a communication link, a control mechanism, a storage mechanism, an output mechanism, and at least one power source configured to operatively power the devices if these do not operate passively. Although various functions that may be performed by devices within the housing mechanism are described herein as mechanisms identified by a name corresponding to the particular function, it is to be understood that any device or devices within the cerebral interface system may be configured to perform one or more of the described functions. Moreover, while the identified functions may be performed jointly or separately within one or more devices within the cerebral interface system, multiple devices may perform the same function, providing a degree of redundancy and robustness. Further, the entire cerebral interface system can be made fully integrated so that any and all functions can occur seamlessly without designated hardware.

A sensing/conditioning mechanism may be used to sense, receive and condition or pre-process signals or other information from the brain and/or body received by way of the communication mechanism. Sensing encompasses any chemical or physical signal that is detectable.

The communication link may be used to communicatively connect one or more devices within a housing mechanism to other devices within the same housing mechanism or external to the housing mechanism, including devices within other housing mechanisms, or devices implanted within or attached to the subject not positioned inside a housing mechanism, or devices external to the subject. This communication link may consist of an internal link connecting devices within the same housing mechanism, and an external link that serves to connect one or more devices within the housing mechanism to one or more devices outside of the housing mechanism. In other words, the communication link allows the creation of a network of devices with components that may be internal and/or external to the subject. Connections may be via conductors (e.g., wires or fiber optic fibers) or wireless (e.g., via radio-frequency "RF" telemetry).

The control mechanism can be used to perform signal and other analytical tasks and may control, assist in, or coordinate the operation of other devices such as the communication link, sensing mechanism, storage mechanism, and/or output mechanism. The analyses tasks may include the execution of closed-loop or open-loop control functions for successful operation of the system, such as those used to monitor, quantify, record, detect, or predict changes in brain and/or body state. The control mechanism, in conjunction with the communication mechanism and the communication link as needed may be configured to transmit signals from the subject's brain and/or body to the network of devices. Further, the control mechanism, in conjunction with the communication link as needed, may be configured to receive signals from the sensors and/or the network of devices, perform analyses of these signals and, using these analyses (e.g., indicating the detection and/or prediction of a brain, body, or organ state change), activate the output mechanism(s) in response thereto.

The storage mechanism provides a means for storing information obtained or generated during the operation of devices within or associated with the bi-directional cerebral interface system. This may include the storage of events (for example, signals, data, samples, logs, etc.) detected, predicted, or quantified by the system, and/or any other information. Such information may be preserved, for example, on a volatile medium, such as a flash ROM, or non-volatile medium for eventual communication to a user of the system.

The output mechanism provides a means for any or all of the devices within the housing or the network of devices to deliver output to the brain and/or body via the communication mechanism, or to output information to the subject, to any other user of the system or to other apparati. Output mechanisms may include, but are not limited to, devices that may be activated by the control mechanism (or any other device in communication with the output mechanism), such as electrodes placed in or over (intracranially, cranially, or extracranially) the brain, or, in or over the spinal cord, its roots or nerves for delivery of electrical currents, catheters connected to a medicament injector such as a pump, a warning mechanism providing any type of sensory stimulus (including light, audio, vibration, or low-voltage stimulation), a mechanism configured to deliver sound, ultrasound, electromagnetic waves, or some other interactive phenomena, including biofeedback. The output mechanism may also be configured to produce thermal changes in brain (e.g., a brain cooling device), spinal cord including its roots or nerves, or other organs, or to provide magnetic stimulation to the brain, other nervous structures, and/or the subject's body.

Means to communicatively connect the brain/organ with devices or apparati and means to communicatively interconnect devices or apparati or connect devices and apparati, can be implemented using the embodiments described herein as needed to perform any and all necessary or desired tasks.

The cerebral interface system also may contain one or more power source mechanisms configured to power devices contained within the housing, or in communication with the network of devices. A power source mechanism or mechanisms may be contained within, or external to, the housing mechanism, or both. The power source mechanism may consist, for example, of a rechargeable battery and may also include an alternate battery to serve as a backup during recharges, or a coil used in RF-coupled recharging in combination with an external charger. The housing mechanism may also be equipped with an access through which the battery may be connected to a re-charger. In one embodiment of the present invention, the outer surface of the housing mechanism may be exposed to the external environment, allowing recharging of, for example, embedded solar energy cells, via exposure to light. One skilled in the art will appreciate that the power source mechanism may be optional in the event that the cerebral interface system consists only of passive devices that do not require an external power source.

The housing mechanism can also serve other functions, such as containing sterile and/or non-sterile chambers that may be externally accessible. Sterile chambers can be used with appropriate fittings/modifications to collect or biopsy brain tissue, meninges or cerebro-spinal fluid ("CSF"), to store drugs/compounds for delivery to the brain, and/or for assaying tissue or CSF for biochemical substrates or cells. A non-sterile chamber, properly isolated from sterile or "clean" parts of the housing mechanism, may contain the power source and have means for external accessibility, such as a removable cap or lid to allow for battery recharging or replacement without requiring surgery. Such cap or lid may, for example, be circular or ovular in shape, may contain hinges, or may be attached with threads or screws in a manner that would allow easy removal and permit a fluid-tight seal upon closing. The housing mechanism may be also used in visualizing or imaging intracranial structures using optical, ultrasound, magnetic, or other means. Additionally, the housing mechanism, or parts of it, may also be used as fiducials to aid in localization of surface or deep brain targets (stereotaxis). It may also be configured with mounts to allow the attachment, engagement, fixation/stabilization of other devices or tools to the housing mechanism as well as their removal. These may include stereotactic frames, reservoir draining and/or replenishing devices, such as a battery recharger and/or device programming or reconfiguring mechanisms. The high stability of the housing mechanism's position in relation to the skull and brain allows for easy, accurate, and reproducible stereotactic or multi-dimensional placement; and/or replacement of probes, sensors, or other devices, including time-dependent positioning. The housing mechanism can serve as a conduit or access for diagnostic, monitoring, or therapeutic elements such as electrode leads, endoscopes, catheters, or ablation tools. The housing mechanism may be equipped with ports to allow direct delivery of drugs or compounds into the meninges, CSF, or brain tissue. The opening and closing of these ports may be controllable and may include self-resealing membranes.

In a preferred embodiment, the housing mechanism includes an inner wall having an inner surface substantially aligned with the inner table of the subject's skull. The inner wall of the housing may include one or more ports such that a connector or connectors of the communication mechanism can extend through the port or ports into the subject's brain. With this arrangement, the sealing mechanism may include a fluid-tight seal between the connector or connectors and the inner wall and/or brain. The sealing mechanism may include or consist of a bio-compatible coating, caulking, and/or a layer of resilient bio-compatible materials such as silicon, polyurethane, or plastic encircling the housing mechanism, etc.

The housing mechanism, in particular an inner wall thereof in its totality or at pre-specified points, may be used for the acquisition of electrical (e.g., EEG, ECoG, EKG), mechanical (e.g., blood or CSF pressure; sound; or ultrasound), biochemical (e.g., glucose concentration), optical (near infrared, fluorescent), or other signals, by embedding the appropriate sensors into the wall or otherwise attaching the sensors to the inner wall. For instance, near infrared sensors may be incorporated into the inner wall of the housing mechanism to optically record cortical activity for monitoring and detection of state changes.

The inner wall of the housing mechanism may be directly used for the acquisition of signals (e.g., electrical currents), a task requiring that the housing mechanism be in close apposition to the source (e.g., in contact with a cortical surface) in order to obtain high quality signals. For this application, the housing mechanism may be configured to include tracks upon which the housing mechanism, or a part thereof, may be mounted so that one or the other may be lowered to touch the cortical surface. The ability to lower or elevate at least one part of the housing mechanism may also allow: (a) more precise alignment of its inner wall with the inner surface of the inner table of the skull to account for regional or inter-individual differences in skull thickness, and (b) improved acquisition of signals or tissue, or (c) delivery of therapies requiring direct contact with the brain. Additional tracks, adjustable threads or screws, and/or slidable plates allow the position of a movable part of the housing mechanism relative to skull or brain structures to be adjusted with three independent degrees of freedom (x, y, z).

Another embodiment of the housing mechanism includes a device positioning mechanism that provides precise x-, y-, and z-axis and angular placement of devices located within the housing mechanism, relative to the skull and brain of a subject. The housing mechanism may further include an internal positioning mechanism used to control positioning of devices or other elements housed within the housing mechanism. The positioning mechanism can be used to adjust the position of a device or sensing element relative to the skull or brain structures. It may also be used to control the vector of access of protruding/retractable probes or sensors, such as a needle or electrode lead, to position them in a manner that allows them to reach their particular target or targets.

To improve fitting and to evenly distribute the pressure exerted by the device on the scalp as well as to improve comfort and decrease the probability of soft tissue erosion, a portion of the housing mechanism may be made of, or incorporate into its structure, soft, pliable, biocompatible material (e.g., silicon), or the housing mechanism may be encased in, or padded/fitted with such material. Constructing portions of the housing mechanism with this type of material can also enable the housing mechanism to better conform to the shape of the subject's skull.

The housing mechanism, which in a preferred embodiment is oval-shaped, may include an outer wall having an outer surface that is substantially aligned with the outer surface of the outer table of the subject's skull. In that case, the housing mechanism may include a flanged edge which is configured to be spaced in abutting engagement with the outer surface of the outer table of the subject's skull. Alternatively, the housing mechanism may comprise both an intraosseous portion, spaced in a cavity in the skull, and/or an extraosseous auxiliary portion that extends tangentially and/or normally outwardly from the cavity formed in the subject's skull. Although herein we shall use the term "auxiliary" for the extraosseous portion of the housing mechanism, this is not meant to convey a master-slave type relationship, nor that devices housed all or in part within the auxiliary portion would have a lesser or subordinate role in the cerebral interface system. An auxiliary portion of the housing mechanism may be either spaced apart from an intraosseous portion of the housing mechanism, removably secured to the intraosseous portion, or removably secured directly to the skull. One skilled in the art will appreciate that all or part of any of the devices described herein as being spaced within the intraosseous portion of the housing mechanism may alternatively be spaced within the auxiliary portion, and devices inside one portion may communicate with devices inside other portions, either uni-directionally, or bi-directionally, via the communication link. Preferably, the auxiliary portion has substantially the same profile as the subject's skull thereunder, with the peripheral edges thereof grading into the outer surface of the subject's skull. The term "housing mechanism" is used herein to generally refer to a structure for device housing comprising one or more intraosseous or extraosseous/auxiliary portions. The term "intraosseous housing mechanism" is used herein to generally refer to an intraosseous portion of a housing mechanism and the term "auxiliary housing mechanism" is used herein to generally refer to an extraosseous auxiliary portion of a housing mechanism.

Although in one embodiment the shape of the intraosseous housing mechanism is cylindrical with an oval-shaped base, the dimensions of dominant non-radial axes of the housing, or curvature radii corresponding thereto, may be made proportional or scaled to the length of the axial and coronal axes of an individual to better distribute forces and decrease potential damage to skull/brain and to the device in case of trauma to the head.

Another embodiment configures an auxiliary portion of the housing mechanism to have a substantially flat extension tangential to the outer table of the skull. This may be useful in cases for which the extra room provided by the tangential auxiliary portion is not needed, but where the protection afforded by the widened exterior needs to be retained to decrease the risk of accidental slippage or internalization of the device into the brain, a likely occurrence in the event of an impact upon a housing mechanism supported only by screws. Such risk is inherent in prior art designs.

The attaching mechanism for the intraosseous and/or auxiliary portions of the housing mechanism may include removable fastening means, such as one or more screws or tracks attached to or advanced into the subject's skull. The intraosseous housing mechanism, auxiliary portion, and removable fastening means are preferably all constructed of titanium or other suitable biocompatible material.

An embodiment of the interface system of the present invention includes an output mechanism configured to include a treatment portion that utilizes a thermally conductive element, which may for example contain coolant or refrigerant, spaced in abutting engagement with a thermally conductive inner wall of the housing mechanism for transferring thermal energy to, or absorbing thermal energy from, underlying tissue. Those skilled in the art can appreciate that transferring thermal energy to, or exchanging thermal energy with, intracranial tissues may also take place through tubes or probes whose length depends on the required application. Appropriate insulation may be provided between the thermally active and inactive elements of the interface and between the interface and the bone and scalp.

Another embodiment of the interface system of the present invention includes an output mechanism configured to include a medicament portion having an inner wall of the housing mechanism with at least one pore structured to administer medicament to underlying tissue disposed in close proximity to the at least one pore. A shutter mechanism with at least one opening corresponding to the at least one pore has open and closed configurations for controlling the administering of the medicament. Based on the disclosure herein, one skilled in the art will appreciate that tubes or microtubes or nanotubes may also be used for delivery of medicament.

Another embodiment of the cerebral interface system of the present invention includes one or more recording and/or stimulating contacts mounted on and extending outwardly from the inner wall of the housing mechanism wherein one or more of the contacts may be a penetrating-type contact, a surface-type contact, and/or a combination penetrating-type/surface-type contact.

One skilled in the art will appreciate that, subject to appropriate shape and size modifications, the housing mechanism and devices contained therein may be spaced within cavities within other non-skull bones of the body as well, e.g., in the vertebral bones to thereby provide an interface between housed devices and the spinal cord or in ribs to provide an interface between the housing mechanism and neighboring organs.

In general, the present invention involves the transformation of a virtual space of the skull or other bones into a real space for the safe and ergonomic placement of a system for interfacing devices to the brain or other organs of a subject and to other devices. The present invention includes, without limitation, improvements in the fields of medicine, neurology, neurosurgery, bioengineering, and biocybernetics, which enable real-time analysis and/or control of biologic signals, such as those related to an EEG signal and/or an ECoG signal of a subject. Such signals can be rapidly, accurately, and automatically monitored, analyzed, transmitted, or stored by the present invention in order to, for example:

(a) monitor, predict, or detect and indicate the occurrence of a normal brain activity, such as drowsiness, and/or an abnormal brain activity, such as an epileptic seizure, in real time or essentially contemporaneously with the arrival of an EEG or ECoG signal at a signal processor;

(b) predict behavioral changes associated with such abnormal activity;

(c) download or telemeter the detection or prediction outputs to devices for warning, logging, and/or storage of data; and/or (d) apply responsive measures to prevent or control such normal and/or abnormal activity in the brain or body of a subject.

The interface system, disclosed herein, provides for the safe, ergonomic, cost-effective and energy efficient implantation of devices for automated sensing, monitoring and control of changes in brain and/or body states, considerably improving the state of the art.

PRINCIPAL OBJECTS AND ADVANTAGES OF THE INVENTION

The principal objects and advantages of the present invention include: providing an interface system that provides convenient access to the brain and/or organ(s) of a subject via a device mountable in a cavity formed in the subject's skull or in other bones or walls; providing such an interface system that includes a housing mechanism, preferably constructed of titanium; providing such an interface system having at least one auxiliary portion of a housing mechanism extending tangentially outwardly from such a cavity, thereby increasing usable space and decreasing risk of brain injury from an impact therewith; providing such an interface system that includes a sealing mechanism for providing a fluid-tight seal between a housing mechanism thereof and the subject's skull; providing such an interface system that may include a control mechanism therein; providing such an interface system that includes a communication mechanism for connecting at least one device inside the housing mechanism to the brain or other organ; providing such an interface system that includes a power source; providing such an interface system with means for lowering and/or raising an inner wall or portions thereof relative to the inner table or the surface of the brain of a subject; providing such an interface system that includes links (wireless or otherwise) for communication between devices in the same or different housing mechanisms or external to the subject; providing such an interface system that includes a control mechanism for activating an output mechanism; providing such an interface system that includes removable fastening means for securement to a subject's skull; providing such an interface system that includes sterile and/or non-sterile compartments which are externally accessible; providing such an interface system that includes means for multi-modular and/or multi-functional capabilities; providing such an interface system wherein devices with different functions and environmental requirements may be housed; providing such an interface system and mechanism that allows replacement of modules therein; providing such an interface system that includes means for allowing adjustments thereof relative to the brain, skull, or scalp of a subject; providing such an interface system that includes a reservoir for controllably administering drugs or other substances; providing such an interface system having means that serve to guide stereotactic placement/replacement of probes and localization of surgical targets; providing such an interface system having means that allow repeated sampling, imaging, or analysis of brain tissue, gases, and/or fluids; providing such an interface system having means that allow recharging of batteries thereof by using solar power; providing such an interface system that can operatively heat or cool tissue in abutting engagement therewith; providing such an interface system that includes means for administering medicament to tissue spaced in close proximity thereto; providing such an interface system that includes a separate auxiliary compartment with a removable lid either secured to or spaced apart from a housing mechanism thereof; providing such an interface system that includes penetrating-type and/or surface-type contacts extending outwardly from a housing mechanism thereof; providing such an interface system that includes a supporting mechanism for precisely displacing a housing mechanism thereof angularly and/or along x-, y-, and z-axes; and generally providing such an interface system that is effective in operation, reliable in performance, capable of long operating life, and particularly well adapted for the proposed usages thereof.

Other objects and advantages of the present invention will become apparent from the following description taken in conjunction with the accompanying drawings, which constitute a part of this specification and wherein are set forth exemplary embodiments of the present invention to illustrate various objects and features thereof.

BRIEF DESCRIPTION OF THE DRAWINGS

FIG. 14 are schematic cross-sectionals view of an embodiment of the cerebral interface system that includes means for conforming the housing mechanism to the shape of the subject's skull, according to the present invention.

FIG. 16 depict various views of an embodiment wherein a portion of the cerebral interface system is attached in moveable engagement with a device positioning mechanism, according to the present invention.

DETAILED DESCRIPTION OF THE PREFERRED EMBODIMENT

Figure 1:
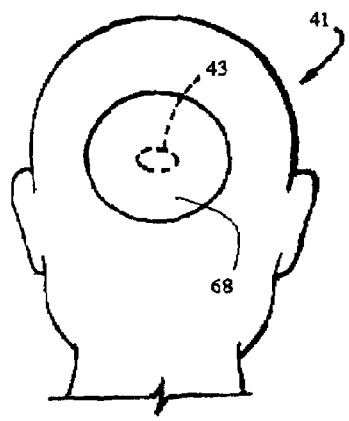
FIG. 1 is a schematic rear view of a subject using a cerebral interface system, according to the present invention.
Figure 2:
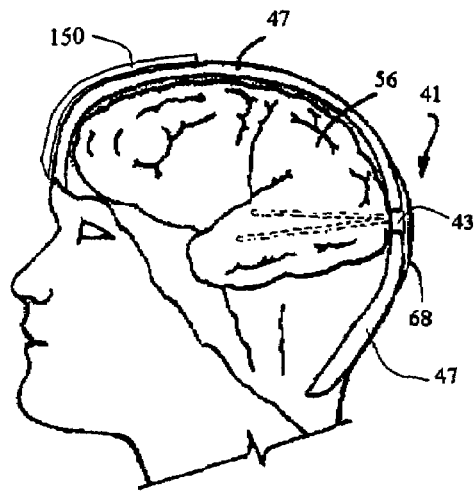
FIG. 2 is a side view of the head of a subject, with portions removed to schematically show the cerebral interface system secured to the skull and sensors inserted into the brain of the subject.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

A detailed description of a prior art system for the prediction, rapid detection, warning, prevention, and control of changes in activity states in the brain of a subject has been previously disclosed in U.S. Pat. No. 5,995,868, issued Nov. 30, 1999 to Ivan Osorio et al, which disclosure is incorporated herein by reference.

Changes in cerebral state are highly correlated with changes in level and activity type in other organ systems, heart for example, and, as such, these signals from such other organ systems may be useful for detection and prediction of changes in brain and/or body state. The signals that may be used instead of, or in addition to EEG and ECoG signals for analysis by components housed within the system include, but are not limited to:

(a) non-electrical cerebral global or regional signals, such as concentrations of glucose, free radicals, metabolic by-products, aminoacids, proteins, neurotransmitters, ions or other substances, or measurements of intracranial pressure, temperature, or indices of metabolic activity, etc.;

(b) cardiovascular signals such as EKG, heart rate, R-R interval and variability, blood flow, blood pressure, etc.;

(c) respiratory signals such as tidal volume, peak-to-peak interval, respiratory rate, etc.;

(d) electrodermal and other DC or AC potentials;

(e) signals representative of concentrations in the blood or other peripheral tissues of gases, substances, or chemicals such as lactic acid, etc.;

(f) signals representative of the level or type of activity of cranial or peripheral nerves, such as frequency and pattern of action potentials for example;

(g) signals related to EMG activity, force, direction, and patterns of limb or body movements; and (h) other signals such as magnetic fields, thermic potentials, recordings from a dynamometer or accelerometer attached to the subject or bed, etc.

It is also important to note that while, for the sake of clarity, descriptions herein primarily involve data from a single sensor, the methods for signal analysis can be simultaneously applied in parallel to signals from several individual sensors and combinations of sensors and different sensor types. It may be desirable, for example, to obtain or analyze a weighted sum of the electrical potentials between a given sensor and other electrical or chemical sensors, or to monitor spatio-temporal correlations of the outputs of multiple sensors or sensor types.

To the extent presently feasible or necessary for a particular application, an interface system 40 of the present invention includes at least one housing mechanism 41 for interfacing with the brain and/or other organs of the subject as generally shown in FIGS. 1 through 19. The housing mechanism 41 generally includes an intraosseous housing mechanism 43 configured and structured to be spaced in a cavity 45 formed in a subject's skull 47; attaching means 53 configured and structured to attach the intraosseous housing mechanism 43 to the subject's skull 47; sealing means 55 structured and configured to provide a fluid-tight seal between the intraosseous housing mechanism 43 and the subject's skull 47, dura mater 139, brain 56, and/or scalp 150; and a communication mechanism 63 configured to communicatively connect the subject's brain 56 to the housing mechanism 41 and/or to at least one mechanism, device, or element 66 housed within the housing mechanism 41. Such mechanisms, devices, or elements 66, sometimes schematically indicated in the Figures using boxes labeled as "D," may be housed, completely or in part, within an intraosseous portion of the housing mechanism 43 and/or an extraosseous auxiliary portion 68, as hereinafter described, and may include but are not limited to: sensing/conditioning mechanisms 70 that may be used to receive and condition or pre-process signals or other information from the brain 56 and/or body received by way of the communication mechanism 63; a communication link 71 having an internal communication link 72 that may be used to communicatively connect one or more devices within the intraosseous housing mechanism 43 to one or more devices within the same housing mechanism 41, and an external communication link 73 that may be used to communicatively link mechanisms, devices or elements 74 external to the intraosseous housing mechanism 43 resulting in a network of devices 80; a storage mechanism 88 that provides a means for storing information obtained or generated during the operation of cerebral interface system 40; an output mechanism 90 that provides a means for any or all of the devices within the network of devices 80 to deliver output to the brain and/or body via the communication mechanism 63 or to output information to the subject or any other user of the cerebral interface system 40; a control mechanism 86 that may be used to perform analytical tasks and may control or assist in operation of other devices such as the communication link 71, sensing mechanism 70, storage mechanism 88 and/or output mechanism 90; a positioning mechanism 98 configured to position all or part of the housing mechanism 41 in relation to the structures of the brain 56 and/or skull 47, in order to control the position of mechanisms, devices or elements 66 housed in part within, or otherwise connected in communication with the housing mechanism 41 or to gain access to intraosseous housing mechanism 43; and a power source mechanism 100 configured to operatively power at least one of the mechanisms, devices, or elements 66. For example, the control mechanism 86 may include a microprocessor spaced within the intraosseous housing mechanism 43 with the power source mechanism 100 configured to operatively power the control mechanism 86 and/or other mechanisms, devices, or elements 66 at least in part contained within the cerebral interface system 40.

The intraosseous housing mechanism 43 generally includes an inner wall 106 having an inner surface 108 generally substantially co-planarly aligned with a surrounding inner surface 110 of the inner table of the subject's skull 47. The primary purpose, for such co-planar alignment of the inner surface 108 with the surrounding inner surface 110 of the subject's skull 47 is to simulate the original physical surroundings of the subject's brain 56 as closely as possible to avoid unnecessary trauma to the subject's brain 56. If desired for a particular application, dura mater 139 may be removed and the inner wall 106, in part or in totality, may be placed in direct contact with the subject's cerebral spinal fluid and/or brain. When in contact with the brain, the inner wall 106 may be configured to minimize trauma to brain 56. This may be accomplished by using biocompatible materials of consistency softer or equal to brain 56, or via hydraulic or other means. Preferably, the intraosseous housing mechanism 43 is constructed of titanium or any other suitable, bio-compatible material having desired physical characteristics. For some applications, it may be desirable for the intraosseous housing mechanism 43 to be oval-shaped, as depicted in FIG. 1, with side angle view depicted in FIG. 2. Given the intra- and inter-individual differences in skull thickness and the need to place, in certain applications, the housing mechanism 41 at prespecified distances from the brain, the cerebral interface 40 will be endowed with means to adjust its total radial thickness; for example, the intraosseous housing mechanism 43 may be moved upwardly or slid into the auxiliary portion of the housing mechanism 68, should this be required to co-planarly align inner surface 108 of the intraosseous portion of the housing mechanism 43, with the inner table of skull 47. Similarly, the intraosseous portion of the housing mechanism 43 may moved downwardly either from the auxiliary portion of the housing mechanism 68 or from brackets mounted on the skull 47 to be in close apposition to the surface of brain 56, if necessary. Those skilled in the art will appreciate that there are many ways in which the radial or vertical position of housing mechanism 41 or its radial thickness may be adjusted, in reference to inner table 110 or brain 56.

If desired, the inner wall 106 may have one or more ports 112 therethrough. The communication mechanism 63 may include connecting means 114 and one or more sensors 66 placed in or around the subject's brain 56, and connected through the port or ports 112 to one or more devices, such as control mechanism 86, contained within the housing mechanism 41. The communication mechanism 63 is configured to allow uni-directional or bi-directional communication between devices placed within the housing mechanism 43 and the brain 56, or other organs. The sealing means 55 is, then, also configured to form a fluid-tight seal between the connectors 114 and the inner wall 106 to prevent leakage of cerebral fluid into the intraosseous housing mechanism 43 or to the outside. If desired, the sealing means 55 may include a bio-compatible coating, such as a layer of resilient plastic encircling the intraosseous housing mechanism 43 and its ports 112, or other suitable arrangement.

Figure 3:
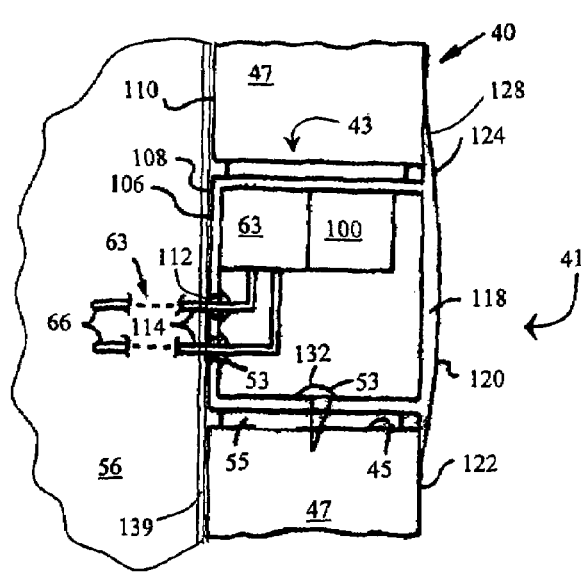
FIG. 3 is an enlarged and fragmentary, schematic view showing a housing mechanism of the cerebral interface system.

The intraosseous housing mechanism 43 may also include an outerwall 118 having an outer surface 120 substantially co-planarly aligned with a surrounding outer surface 122 of the subject's skull 47, as indicated in FIG. 3. In that event, the intraosseous housing mechanism 43 preferably has a flanged edge 124 configured to be spaced in abutting engagement with the outer surface 122 of the subject's skull 47.

Figure 4:
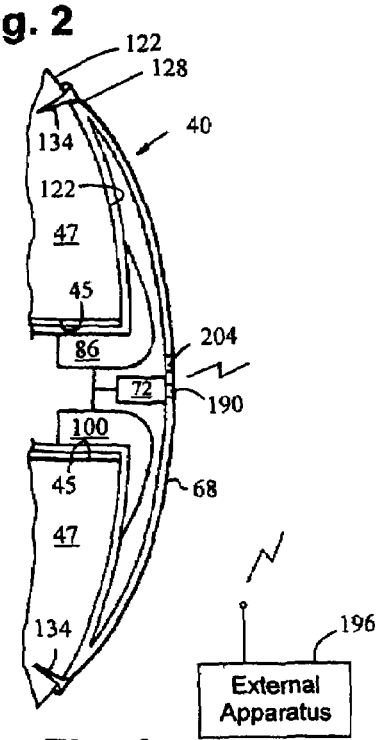
FIG. 4 is an enlarged and fragmentary, schematic view showing the auxiliary portion of the housing mechanism as part of the cerebral interface system.

Alternatively and/or additionally, the housing mechanism 41 may include an auxiliary portion 68 that extends tangentially outwardly from the cavity 45 formed in the subject's skull 47. Preferably, the auxiliary portion 68 of the housing mechanism 41 has substantially the same profile as the subject's skull 47 thereunder, with a peripheral edge 128 thereof approximately grading into the outer surface 122 of the subject's skull 47, as depicted in FIG. 4. The auxiliary portion 68 of the housing mechanism 41 may be hollow such that at least a portion of the control mechanism 86 and/or the power source 100, for example, may be spaced within the auxiliary portion 68, as depicted in FIG. 4. The auxiliary portion 68 of the housing mechanism 41 is also preferably constructed of titanium or any other suitable, bio-compatible material having desired physical characteristics. One skilled in the art will appreciate that any of the mechanisms, devices or elements 66, or any portions thereof, that can be spaced within the intraosseous portion 43 of the housing mechanism 41 may alternatively be spaced within the auxiliary portion 68.

Figure 5A:
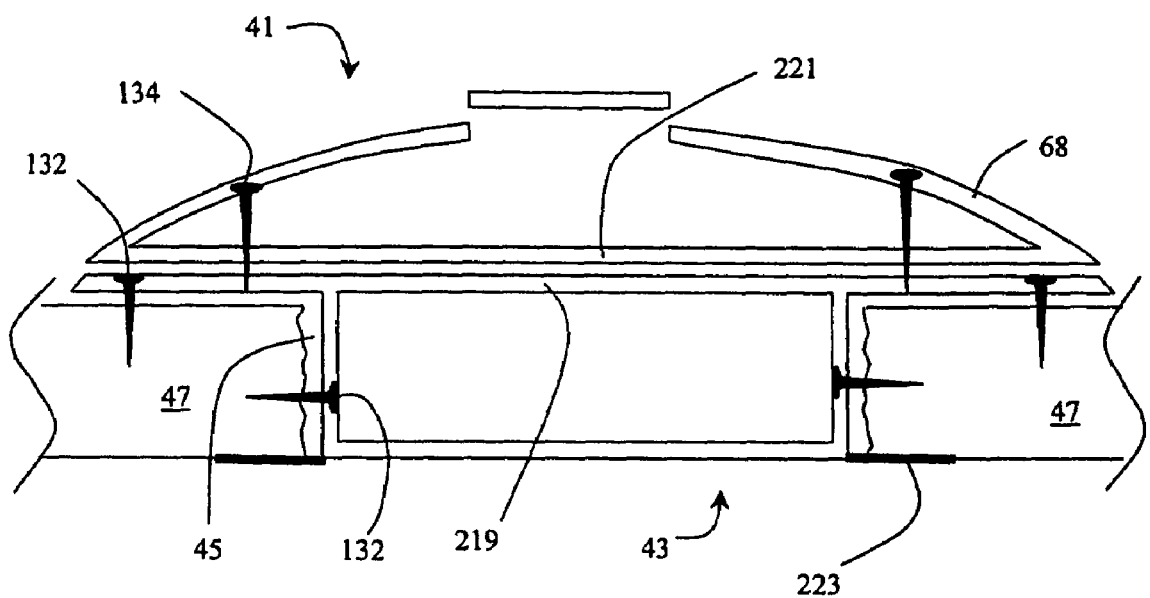
FIG. 5 shows schematic cross-sectional views of an embodiment of the cerebral interface system that includes removable anchoring means and configurations to enable easy access between auxiliary and intraosseous housing portions or combinations thereof, according to the present invention.
Figure 5B:
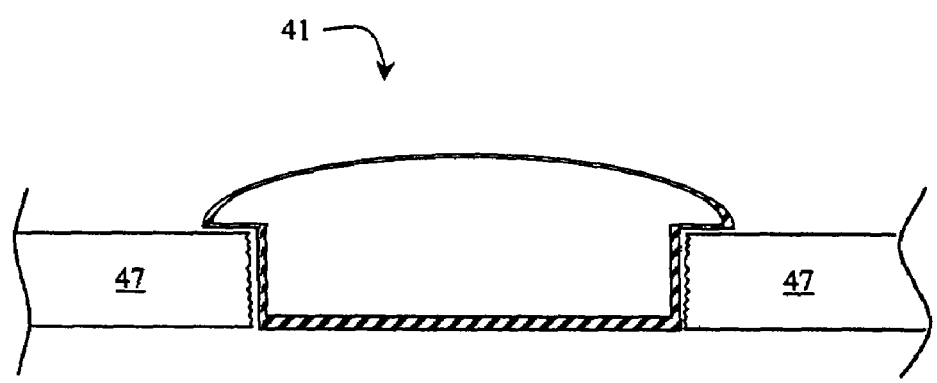

The attaching means 53 generally includes removable fastening means 132, such as one or more screws for example, as depicted in FIG. 3, wherein the fastening means 132 is advanced into the subject's skull 47 to secure the intraosseous housing mechanism 43. The attaching means 53 for applications utilizing the auxiliary portion 68 of housing mechanism 41 as part of the cerebral interfacing system 40 may include fastening means 134, as depicted in FIG. 4, for attachment to the subject's skull 47. The auxiliary portion 68 may be separated by one or more partitions 219, 221 from the intraosseous portion 43 of housing mechanism 41 and removably connected thereto as schematically illustrated in FIG. 5A, or can be combined without such partitions as illustrated in FIG. 5B. One skilled in the art will appreciate that there are numerous other configurations utilizing various partitions of the interior space of the housing mechanism 41 dependent upon the particular application(s) for which it is used. The intraosseous housing mechanism may also be equipped with one or more brackets 223 that may be extended tangentially along the inner table of the skull 47 to assist in securing the housing mechanism 41 in place and avoiding accidental dislodgement. These brackets may be configured with a spring-loaded mechanism to extend/snap into place at the point when the housing mechanism 41 has been lowered to the proper depth, in alignment with the inner table of the skull 47. One skilled in the art will appreciate that the housing mechanism may be further configured with a range/distance sensing device that can determine precise distance from the bottom surface 108 of the housing mechanism 41 to the surface of the brain 56 or dura 139.

Figure 6A:
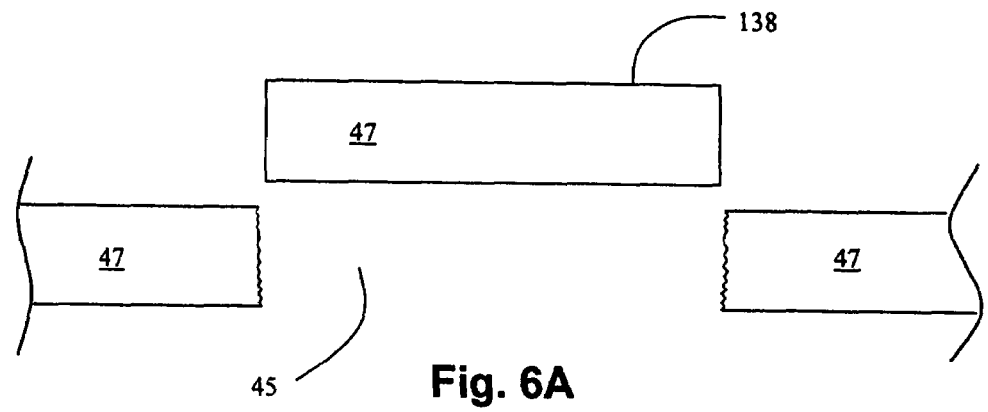
FIG. 6 shows schematic cross-sectional views of an embodiment of the cerebral interface system showing a section of the skull that is removed, populated with one or more housing mechanisms, and replaced so as to function as a cerebral interface system, according to the present invention.
Figure 6B:
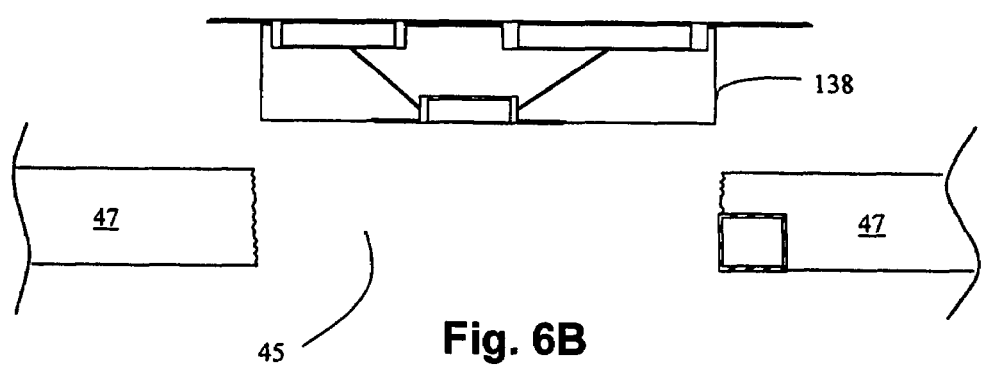
Figure 6C:
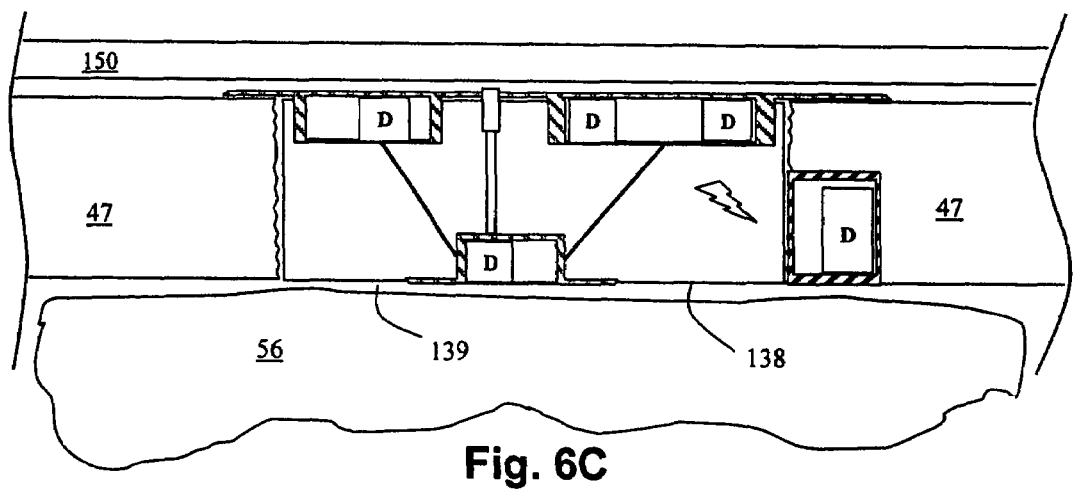
Figure 7:
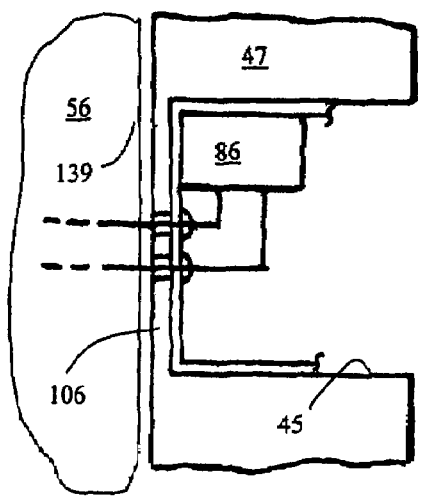
FIG. 7 is an enlarged and fragmentary, schematic view showing a portion of the cerebral interface system implanted in the subject's skull.

The auxiliary housing mechanism 68 serves to both protect the brain 56 and to increase the capacity of the interface system 40 for housing devices. The housing mechanism 41 may be manufactured of any material with suitable strength and bio-compatibility to serve as a safe replacement for any removed bone. Alternatively, the bone portion 138 of the skull 47 removed in a craniotomy, or a suitable synthetic skull portion substitute thereof, may be populated with one or more housing mechanisms 41 and then replaced back into its original position and anchored in place to perform the functions of the invention, as illustrated in FIG. 6A-C. The thickness of the intraosseous housing mechanism 43 may range from being approximately equal to the thickness of the bone 138 of the skull 47 that it replaces to a thickness as large as that dictated by the elastic properties of the scalp tissues. Depending on the size and complexity of the miniaturized electronics, the walls of the intraosseous housing mechanism 43 may be flat and parallel or may be convex and follow the geodesics or other smooth curves that interpolate the boundary of the skull 47 surrounding the cavity 45 and/or the peripheral edge 128 of the auxiliary housing mechanism 68. The housing mechanism 41 may be implanted to either leave some skull bone 47 between the inner wall 106 and the dura 139 and brain 56 as depicted in FIG. 7, or in direct contact with the dura 139 or brain 56 as depicted in FIG. 3. Preferably, an overall shape for the housing mechanism 41 can be selected which is not only large enough to house the necessary components, such as miniaturized electronics, telemetry systems, magnetic stimulators, coils, etc., for example, but is also ergonomic.

Some of the benefits provided by the auxiliary housing mechanism 68 extending tangentially outwardly from the cavity 45 formed in the subject's skull 47, versus an intraosseous housing mechanism 43, include:

(a) the potential for increased interior volume of the housing mechanism 41 thereby enabling additional or larger devices to be housed therein, and (b) preventing the intraosseous housing mechanism 43 from being forced into the brain 56 in the event of an impact to the subject's head.

In addition, the intraosseous housing mechanism 43 may contain an energy-dissipating or absorbing mechanism, may be constructed using energy-dissipating or absorbing material, or have an energy-dissipating or absorbing design such as a "crumple zone" that helps to prevent damage to the brain, head, or housed devices due to shock or head trauma. The housing mechanism 41 may be configured to provide insulation from electrical, magnetic, radio-frequency or other types of interference. The housing mechanism 41 may also provide a means for brain pressure control, such as a shunt, in order to maintain a desired level of internal pressure and to allow release of fluid in the event of fluid accumulation, including hydrocephalus and brain edema.

Figure 8A:
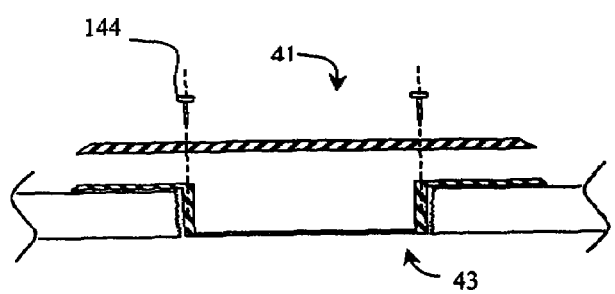
FIG. 8 shows schematic cross-sectional views of embodiments of the cerebral interface system wherein the housing mechanism, or a compartment thereof, contains a ledge extending outwardly therefrom and/or a removable covering thereof, according to the present invention.
Figure 8B:
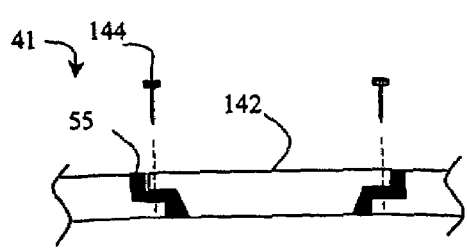
Figure 8C:
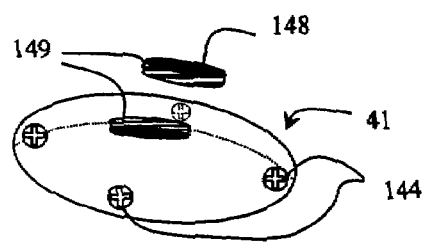
Figure 9A:
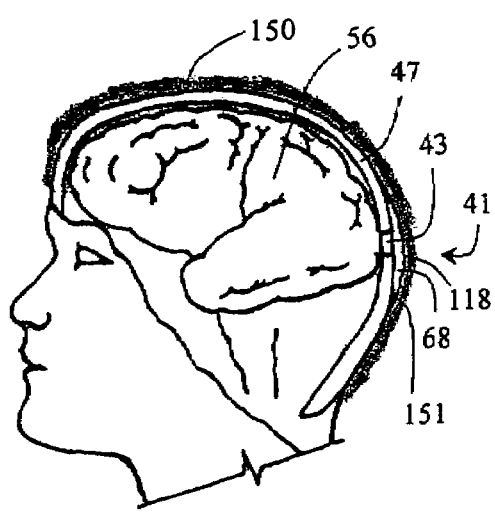
FIG. 9 shows schematic cross-sectional views of an embodiment of the cerebral interface system that includes a scalp tissue pedicle, according to the present invention.
Figure 9B:
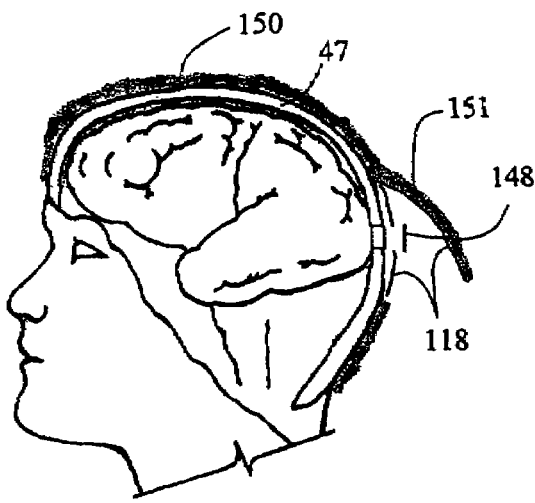
Figure 10A:
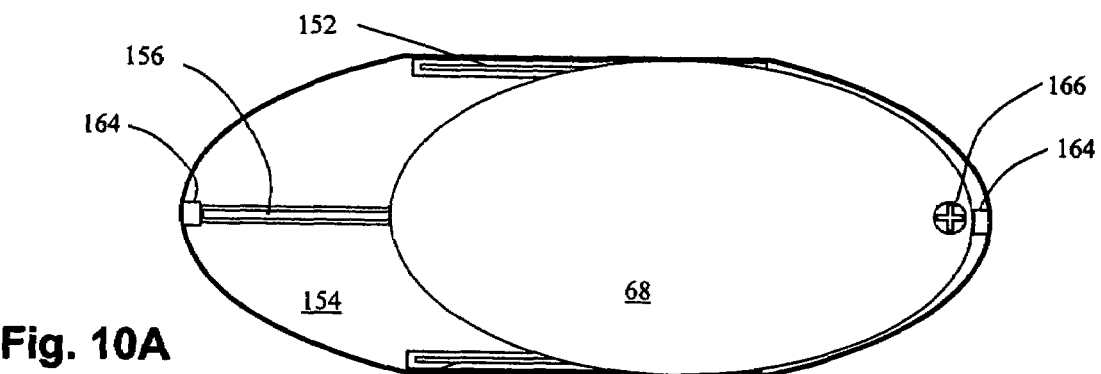
FIG. 10 shows schematic views of means for displacing an auxiliary portion of a housing mechanism to obtain access to the intraosseous portion of the housing mechanism, according to the present invention.
Figure 10B:
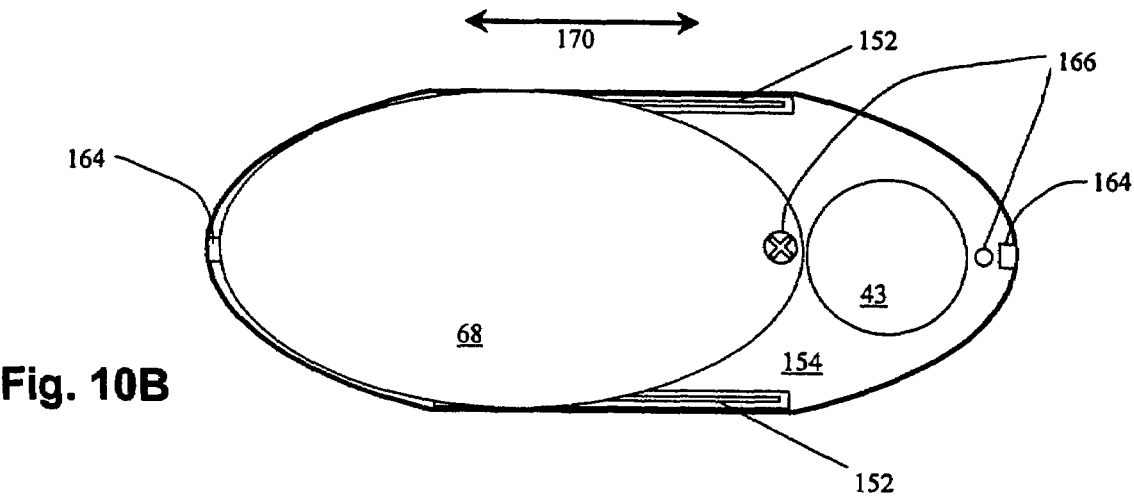
Figure 10C:
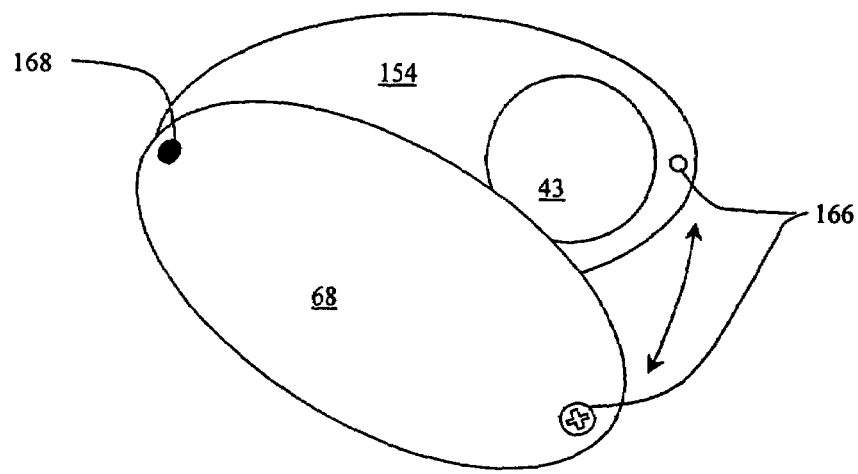
Figure 10D:
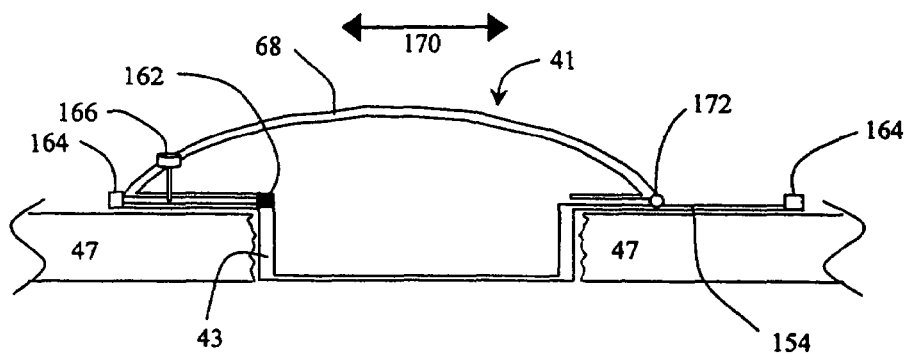
Figure 10E:
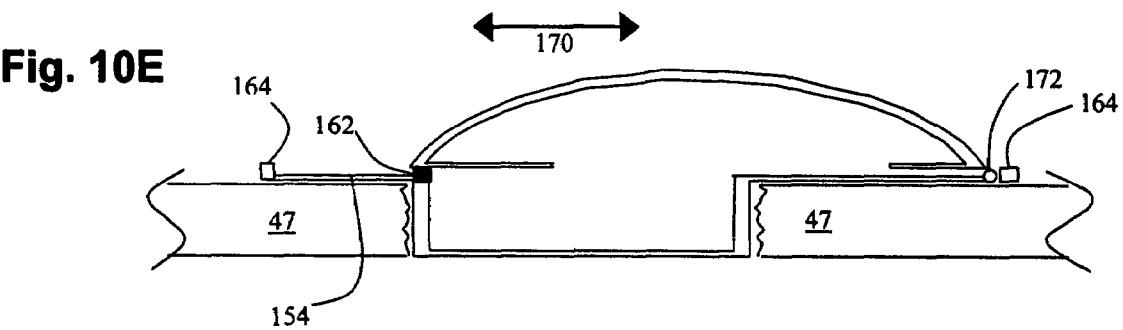
Figure 10F:
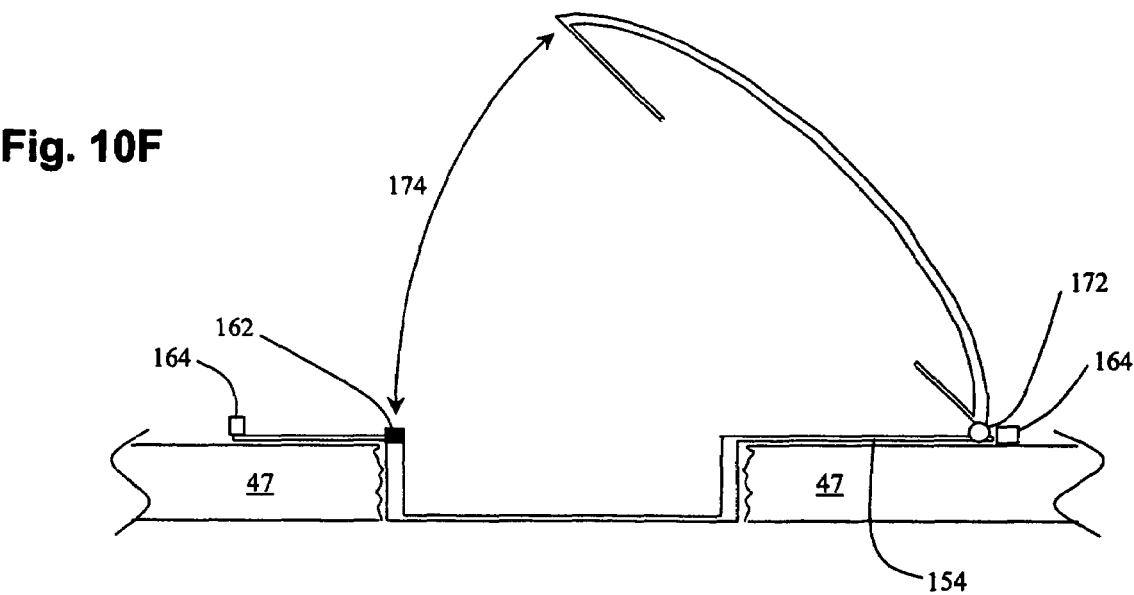

The housing mechanism 41 may be configured to include a portion that is easily removable without invasive procedures. For example, the auxiliary housing mechanism 68 may be removable from the intraosseous housing mechanism 43. In another embodiment of the present invention, the auxiliary housing mechanism 68 may contain one or more accesses that allow internal components thereof, such as a battery 140, to be replaced within the housing mechanism 41 without having to resort to surgical procedures, or with only minor procedures such as a small incision through the scalp. Such accesses may, for example, contain a portion that is exposed, so that direct access to the inside of the housing mechanism 41 may be obtained without surgery, such as that shown in FIGS. 8A-C. For example, FIG. 8B illustrates a removable hatch or cap 142 not covered by the scalp, along with flush-mounted screws 144 to affix the cap 142 to housing mechanism 41; a seal 55 is provided to prevent leakage and contamination. FIG. 8C shows another embodiment of a removable cap 148 having threads 149, to make a threaded connection to the housing mechanism 41 (seal not shown). FIG. 9 illustrates accessibility to the housing mechanism 41, including access to intraosseous housing mechanism 43 and/or auxiliary housing mechanism 68, obtained by creating a scalp tissue pedicle 151 in scalp tissue 150 which is attached to and covers (for cosmetic purposes) the outer surface of outer wall 118 of the housing mechanism 41. A part of outer wall 118 of the housing mechanism 41 may be hinged at one end so the pedicle 151 and the outer wall 118 can be opened as one for easy access to the interior contents thereof, for example by use of a removable hatch or cap 148. When outer wall 118 is closed, the pedicle lies in close apposition to the surrounding scalp from which it has been partially cut; a portion of the pedicle remains uncut from the scalp to ensure blood supply and its viability.

FIG. 10 illustrates alternative embodiments of the housing mechanism 41 that provide easy but secure access to the interior of portions of the mechanism. FIG. 10A illustrates a top view of a modified embodiment wherein the auxiliary housing mechanism 68 may be movably mounted on a ledge or platform 154 that includes a track system consisting of a central track 156 and parallel tracks 152 to tether and guide the auxiliary housing mechanism 68 as it is displaced along the platform 154 in order to expose one or more chambers within the intraosseous housing mechanism 43. Platform 154 is affixed to the outer surface 122 of the subject's skull 47. FIG. 10B shows the housing mechanism 68 after it has been displaced to fully expose the top of the intraosseous housing mechanism 43, following movement in the direction indicated by numeral 170. In these embodiments, elements such as a spring-loaded latch 162, stopping mechanism 164, and/or lockable latch mechanism 166 may be utilized to provide easy but secure access to devices housed in the intraosseous housing mechanism 43 situated thereaneath, while ensuring that the auxiliary housing mechanism 68 is not accidentally displaced, thereby inadvertently exposing intraosseous housing mechanism 43. FIG. 10C discloses another embodiment in which the auxiliary housing mechanism 68 is rotationally displaced in the plane tangential to the platform 154 around a pivoting mechanism 168. FIGS. 10D-F disclose side angle views of another embodiment of the present invention wherein the auxiliary housing mechanism 68 is displaced along the platform 154, as indicated by the arrow designated by the numeral 170 shown in FIG. 10D. The movement 170 is continued until the stopping mechanism 164 is reached at which point the spring-loaded latch mechanism 162 engages and ejects the outer portion of the auxiliary housing mechanism 68 in accordance with the rotational characteristics of hinge 172, as indicated by the arrow designated by the numeral 174. As will be appreciated by one skilled in the art, the spring-loaded latch mechanism 162 may include a safety lock or lockable latch mechanism 166 illustrated in FIG. 10D to prevent inadvertent or unauthorized access to the underlying intraosseous housing mechanism 43. Each of the embodiments depicted in FIGS. 10A-F has certain advantages over the others, which may be exploited according to the application and characteristics of the size and shape of subject's skull.

Figure 11:
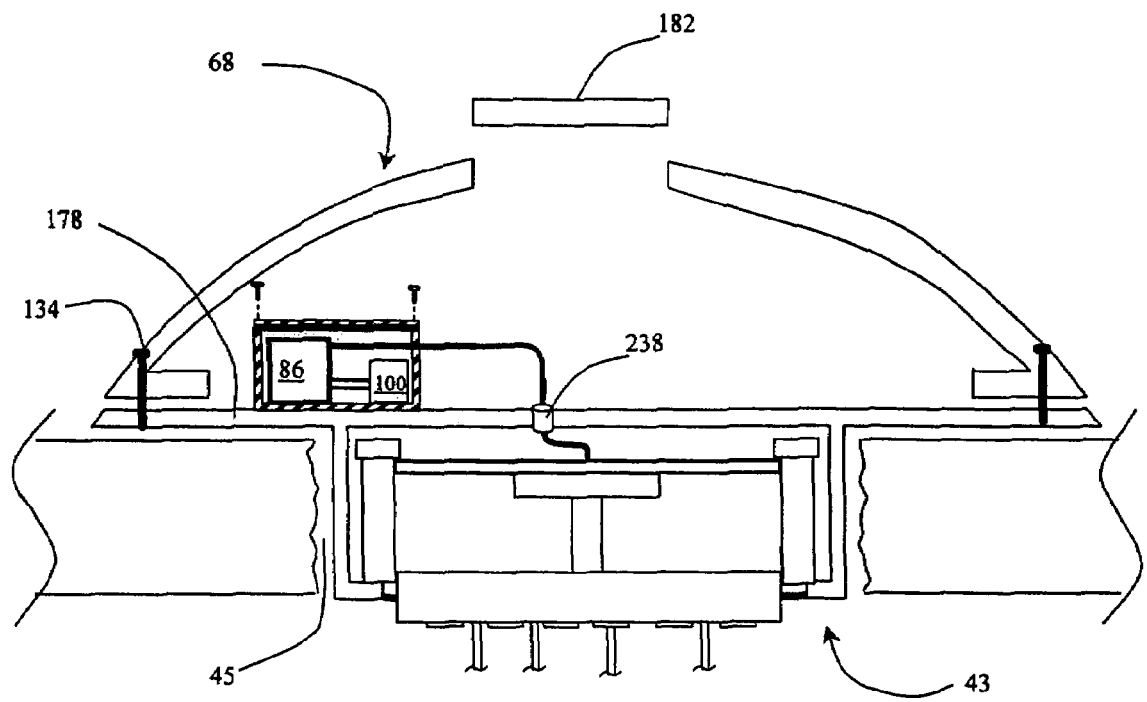
FIG. 11 is a cross-sectional view of a chamber within the cerebral interface system showing a removable cap thereof, and placement of the chamber within the auxiliary portion of a housing mechanism, according to the present invention.

In some applications of the present invention, it may also be desirable to removably secure the auxiliary housing mechanism 68 to, and extending outwardly from, the intraosseous housing mechanism 43 as depicted in FIG. 11. This may be accomplished, for example using removable screws 134 connecting auxiliary housing mechanism 68 to a ledge 178 extending from intraosseous housing mechanism 43. The auxiliary housing mechanism 68, which may contain various components of the system 40 as described herein, such as a power source mechanism 100 and control mechanism 86 as illustrated in FIG. 11, may include one or more removable lid(s) 182 for access to those components as needed. For some applications, it may be desirable to secure the auxiliary housing mechanism 68 to the subject but not secure the auxiliary housing mechanism 68 to the intraosseous housing mechanism 43.

Figure 12A:
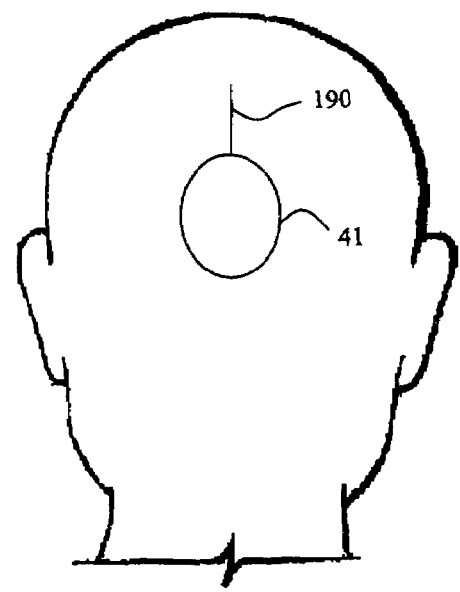
FIG. 12 are schematic rear views of a subject using the cerebral interface system having one and two interconnected housing mechanisms of the cerebral interface system, respectively, each view having an antenna disposed, under, in, or over the scalp of the subject, according to the present invention.
Figure 12B:
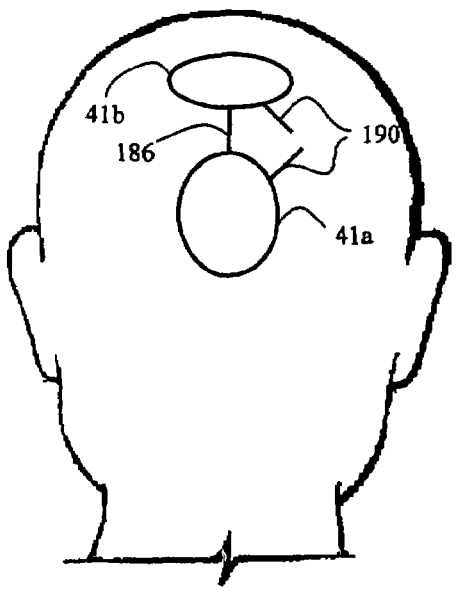

It is also to be understood that some applications of the cerebral interface system 40 may require that more than one housing mechanism 41 be implanted in the skull 47 of the subject. A single housing mechanism is illustrated in FIG. 12A, while multiple housing mechanisms (e.g., two) are depicted by numerals 41a and 41b in FIG. 12B and illustrated schematically in FIG. 13A. In that event, it may be desirable to interconnect the contents of the housing mechanisms 41a, 41b by an interconnection 186 comprising one or more conductors/wires or channels. The devices may be also communicatively connected in a wireless manner via a communication link 71 to each other, to other devices within other housing mechanisms 41, or to devices not contained in or attached to any housing mechanism (e.g., implanted within the subject, attached to the subject, or external to the subject).

Further, the interconnection 186 may be configured to provide an antenna arrangement 190 as necessary to communicatively connect housing mechanisms 41a, 41b with each other and with other apparati. In the case of a wired connection between housing mechanisms 41a, 41b placed in different locations on the subject's head, a groove may be formed into the surface of the skull 47 if desired to nestle the interconnecting cable 186, to minimize the probability of cable breakage. When multiple housing mechanisms are utilized, they may need to be installed over skull regions of different thickness and curvature. To better conform a cluster of housing mechanisms to the local geometry of the skull 47, these multiple housing mechanisms, denoted here by numerals 41a, 41b, and 41c, may have hinged connections 242 or flexible connections 243, as illustrated in FIGS. 14A-E. Those skilled in the art will appreciate that other means of conforming the housing mechanisms to the local shape of the skull are possible and available. The present invention enables one to safely place devices in the skull 47, or in a cavity 45 within the skull, by taking advantage of a virtual space, which consists of the actual width or thickness of the skull 47 and the elasticity of the overlying scalp. The width or thickness of the human skull 47, depending on location, generally ranges between 4-10 millimeters. The virtual space is created by carving out only the diploe and a corresponding portion of the outer table (partial craniotomy), or by removing corresponding portions of both the inner and outer tables of the skull 47 (craniotomy). The diameter or dimensions of an opening so created may be as small as necessary but generally not larger than approximately 4×5 centimeters in order to minimize the risk of necrosis of the surrounding bone to which the housing mechanism 41 is attached, such as by screws, glue or other suitable means. The location of a single cavity or multiple cavities 45 in the skull 47 to receive the intraosseous housing mechanism 43 containing the necessary electronics in a given subject can be dictated by the medical application, anatomical and functional considerations, the judgment and skill of the surgeon, and cost/manufacturing considerations. The locations of the housing mechanisms depicted in the figures in this specification may or may not reflect the site where they will be placed for any particular application. Simply stated, the housing mechanism 41 is intended to house electronic or other devices on and in the skull 47 without impinging on or distorting the underlying structures including the brain 56, or altering the protective environment thereof.

Figure 13A:
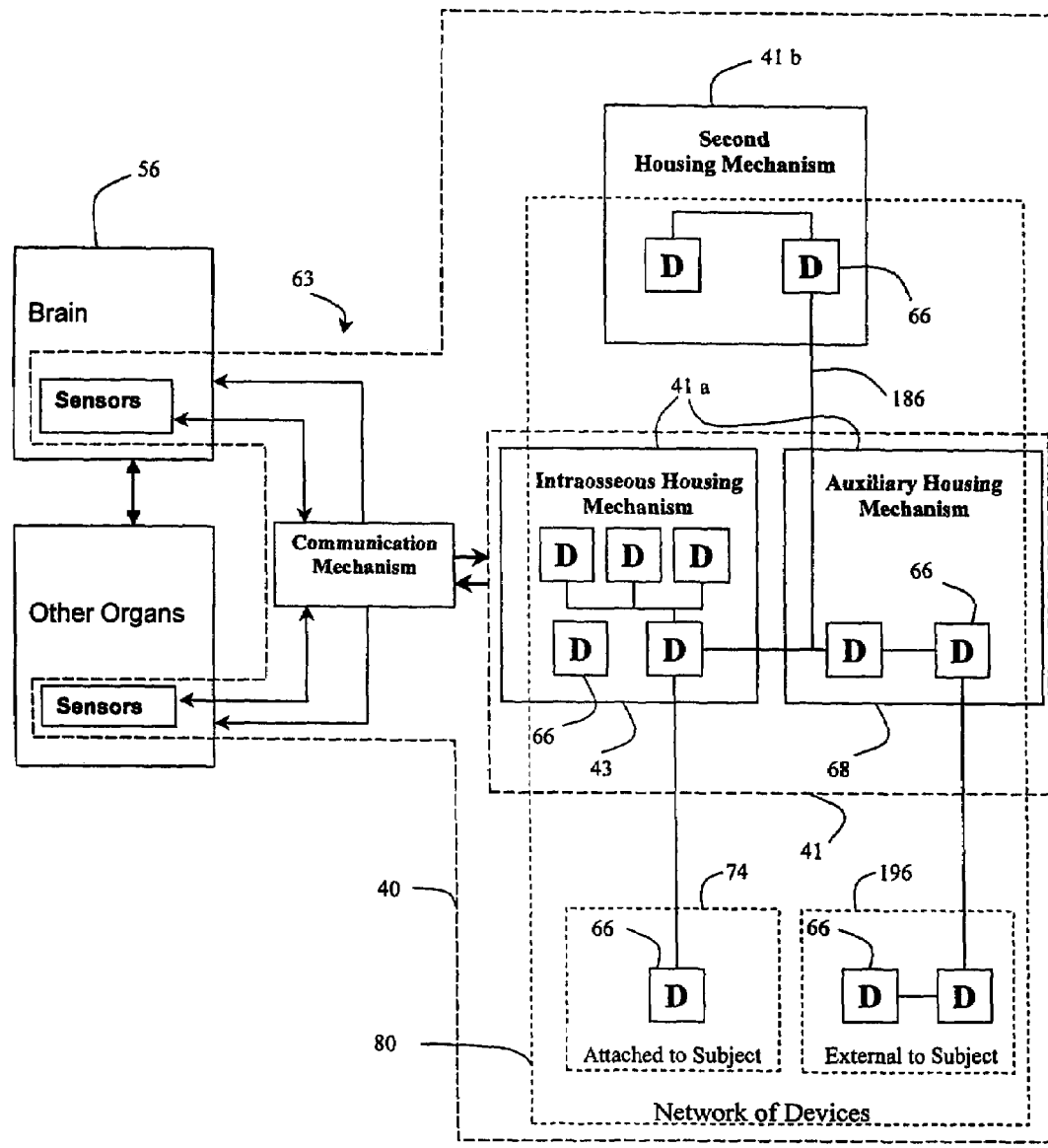
FIG. 13 are schematic views of the cerebral interface system illustrating the various components thereof that may be present according to the present invention.
Figure 13B:
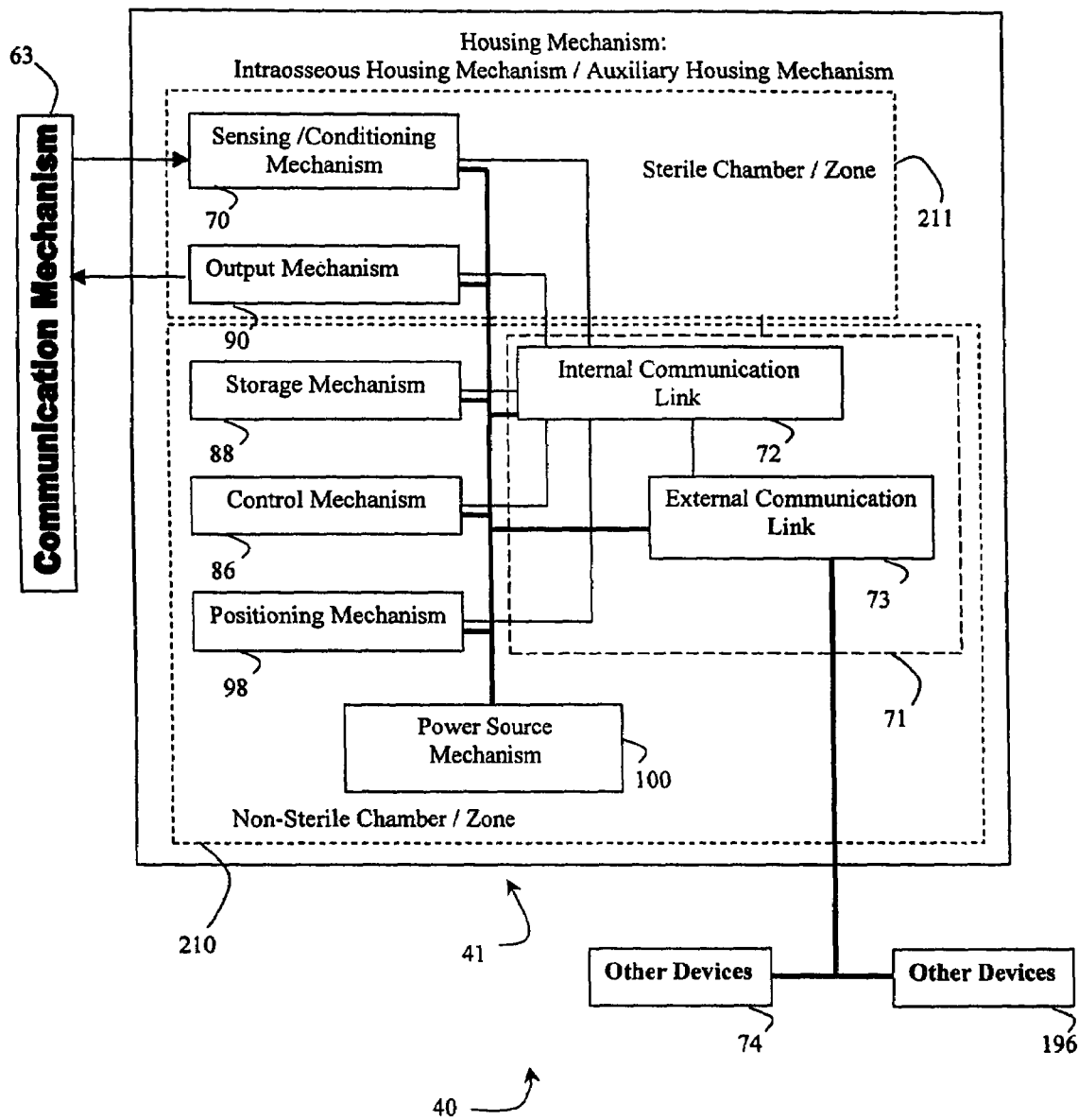
Figure 15A:
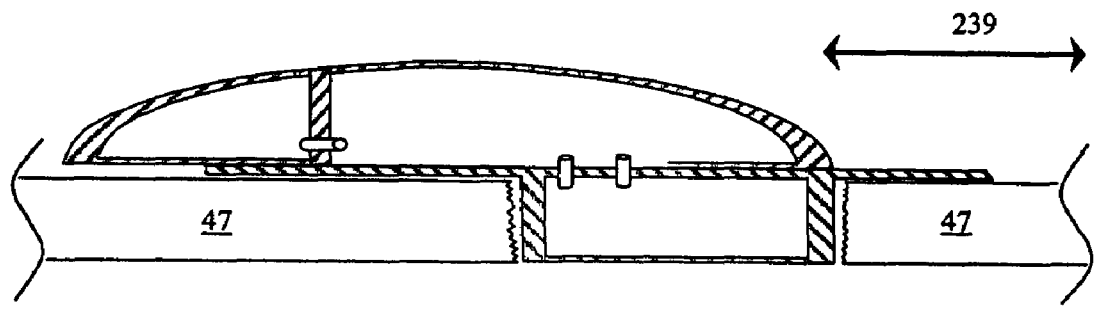
FIG. 15 is a schematic cross-sectional view of an embodiment of the cerebral interface system that includes one or more accessible sterile or non-sterile chambers and ports for their interconnection, according to the present invention.
Figure 15B:
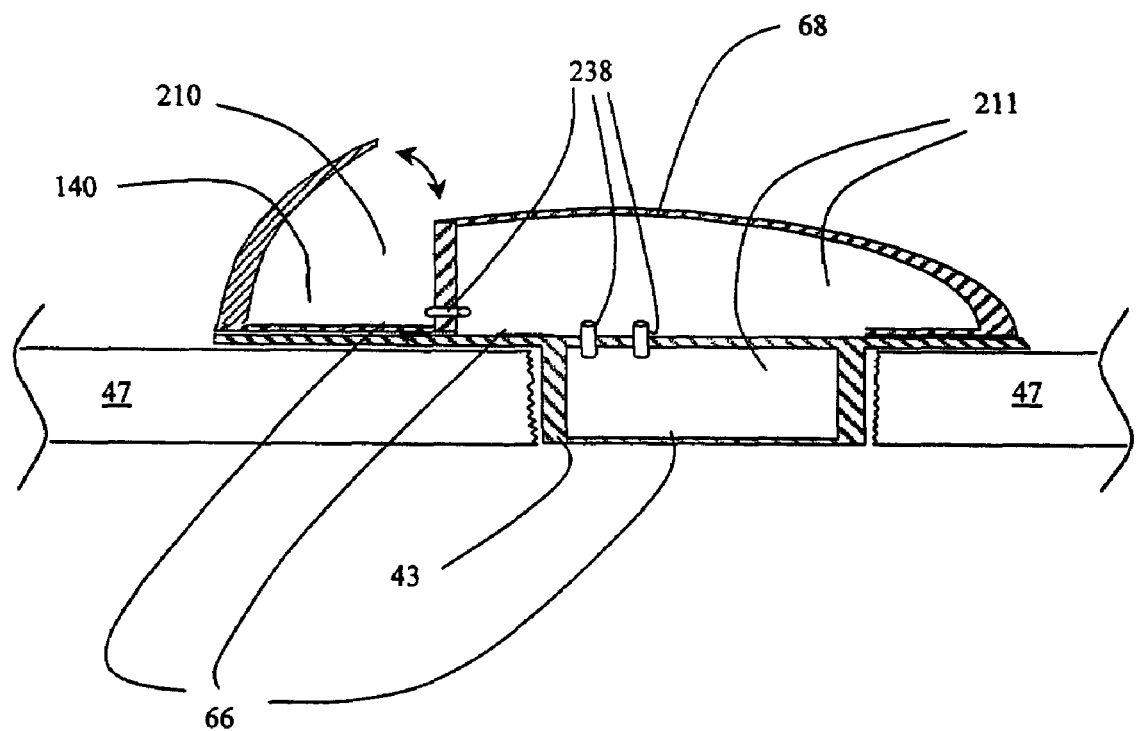

The communication link 71 of the interface system 40, as schematically represented in FIG. 13, may be configured to connect one or more devices such as, for example, the control mechanism 86 in wired or wireless communication with apparatus 196 external to the subject shown in FIG. 13A. For example, an antenna arrangement 190 as shown in FIG. 4, may be used in a manner as known to those skilled in the wireless communication art. In that case, the control mechanism 86, in conjunction with the communication mechanism 63 and the communication link 71, is configured to transmit signals from the subject's brain 56 to the external apparatus 196, wherein the external apparatus 196 is configured to detect, predict, quantify, log, warn and/or provide control of brain state whether normal or abnormal. For some applications, it may be desirable to embed a portion of the antenna arrangement 190 in the scalp of the subject, in a wall of the intraosseous housing mechanism 43 or auxiliary housing mechanism 68, or in a groove in the skull 47 under the subject's scalp, as indicated in FIG. 12A.

The attaching/fastening means 53, 134 for securing the housing mechanism 41 to the skull 47, the body of either the intraosseous housing mechanism 43, or auxiliary housing mechanism 68, may serve as, or be equipped with, one or more antennae 190 for use as a communication link 71 to communicatively connect for example via telemetry, one or more devices contained within the housing mechanism 41 including the auxiliary housing mechanism 68 with additional devices as indicated by numeral 66 either implanted within or attached to the subject as indicated by numeral 74 or external to the subject as indicated by numeral 196. As designated by numeral 66 in FIG. 13 such additional devices may be contained within the same housing mechanism, contained within a separate housing mechanism, may be implanted within the subject, or may be portable and disposed externally to the subject.

Alternatively, the control mechanism 86, in conjunction with the communication mechanism 63, may be configured to operatively detect, predict, quantify, log, warn and/or control or treat normal and/or abnormal brain activity of the subject without the need for external apparatus. In that event, the control mechanism 86 may be configured to, upon the detection or prediction of abnormal brain activity of the subject, automatically and operatively activate an appropriate output mechanism 90 in response thereto. It is to be understood that, even if such self-contained configuration is utilized for a particular application, it may be desirable to selectively access the control mechanism 86, such as through access terminals 204 in FIG. 4, to ascertain a status of the housing mechanism 41, or devices, mechanisms, or elements made part of cerebral interface system 40, that are communicatively connected to housing mechanism 41, and/or information contained within the cerebral interface system 40, such as the present or past state of the organ and subject.

The output mechanism 90 and the control mechanism 86, in conjunction with the external communication link 73, may be configured to communicate with the external apparatus 196 or any other devices within the network of devices 80 connected by the communication link 71, in order to detect, predict and/or provide treatment for normal and/or abnormal brain activity of the subject, and, in response to such output signals indicating such detection, prediction and/or treatment, to activate an appropriate output mechanism 90 in response thereto. For example, the output mechanism 90 may simply comprise a device, preferably separately powered to conserve power source 100, to alert the subject, or it may comprise an electrical stimulator connected via one or more of the connectors 114 to elements 66, such as electrode contacts, appropriately positioned to apply an electric current, etc., directly to the subject's brain 56.

The wall or walls of the housing mechanism 41 may be constructed of opaque material. It is to be understood, however, that at least a portion of the wall or walls of the housing mechanism 41 may be constructed of a material or materials that are translucent, transparent, semi-transparent, non-attenuating, or partially attenuating for delivery of sound, ultrasound, electromagnetic waves, or other interactive phenomena therethrough directly to the brain of the subject, or for recording of waves in the light spectrum such as near infrared. The outer wall 118 of the housing mechanism 41 may also be configured to be transparent or translucent to allow the passage or light from the environment into solar power cells which may be placed on or near its outer surface 120 to provide a renewable power source for devices housed within the housing mechanism 41.

One skilled in the art will appreciate that the disclosed power source mechanism 100 is optional, in that the housing mechanism 41 may house passive devices that function without need for a power supply. The housing mechanism 41 may also contain one or more coils that can be used for battery recharging, magnetic stimulation, or magnetic field detection. A non-sterile chamber, designated by numeral 210 in FIG. 15, which may be exposed to the external environment and is properly isolated from sterile or "clean" parts of the housing mechanism 41, may contain the coils or other elements of the power source mechanism 100, which chamber 210 may be configured to provide means for easily accessing those elements, such as via one or more hinged or removable caps or lids, as designated by numerals 142 and 148 in FIGS. 8B,C and 9B and by numeral 182 in FIG. 11, thereby allowing for battery recharging or replacement, without requiring surgery or with only a small incision.

In one embodiment, a portion of the scalp 150 covering housing mechanism 41 may be removed exposing the outer surface 120 of the housing mechanism 41 thereby obviating the need for surgical incisions to gain access. In this case, the housing mechanism 41 may be further enlarged to align its outer surface 120 with the outer surface of the remaining scalp 150. The exposed outer surface 120 of housing mechanism 41 may be covered with an artificial scalp-like material for cosmetic purposes. Those skilled in the art will appreciate that in certain cases, it may be desirable for the housing mechanism 41 to replace large portions of the skull such as half of the skull (hemicranium), or the entire skull above or beyond a prespecified axial, sagital, or coronal plane. In these cases the housing mechanism 41 may include several removable caps or lids 182 or hinges 172 (see FIG. 10 F) to provide rapid access to devices populating housing mechanism 41.

It is to be understood that the housing mechanism 41 may be equipped with various types of sensors/sensing devices designed to sense electrical, chemical, mechanical, thermal, magnetic, optical, or other activity indicative of brain, organ, or body state. Such devices may either protrude from the inner wall 106 of the housing mechanism 41, be flush with the inner wall 106, or the inner surface 108 or be receded from the inner wall 106 or from the inner surface 108. Useful examples of sensing devices that can be used alone or in combination may include:

(a) an array of one or more platinum-iridium disk contacts on the inner surface 108 of the intraosseous housing mechanism 43 that may be either epidural or subdural, (b) intracortical needle-type leads with either single or multiple contacts protruding into the subject's brain 56, (c) the inner wall 106 or inner surface 108, or one or more portions thereof, of the intraosseous housing mechanism 43 may itself be used as an electrode, thermal conductor, or other type of sensing device, and (d) the inner surface 108 may be porous or contain valves, probes, and/or catheters or tubes, any of which may be controllable and used to collect samples such as spinal fluid, blood, tissue, cells, or gases, and/or deliver chemicals or medicaments to the brain or organs.

For example, a modified embodiment of the present invention includes a plurality of sensing and/or delivery (e.g., electrically stimulating) elements 216 positioned on the inner wall 108 of the intraosseous housing mechanism 43, as depicted schematically in FIG. 16A, to provide three-dimensional multi-site, multi-modal capabilities for detection and control of brain state changes as taught in pending U.S. Pat. No. 7,006,859 of Ivan Osorio et al, issued Feb. 28, 2006 and entitled "Unitized Electrode with Three-Dimensional Multi-Site, Multi-Modal Capabilities for Detection and Control of Brain State Changes," which is incorporated herein by reference. The recording and or stimulating contacts 216 may include one or more penetrating-type contacts 218, surface-type contacts 220, or combination surface/depth contacts 228. Each of the elements 216 are connected via conductors 222 to one or more components 224 in the housing mechanism 41 as appropriate, as hereinbefore described. Insulating material 226 is interposed between each of the contacts 216 and the inner wall 106, as shown in FIG. 16B as hereinbefore described, in order to insulate and isolate (e.g., electrically, thermally, etc.) the contacts 216 from one another, as well as from the inner wall should this be made of electrically or thermally conductive materials.

The distal end of one or more of the surface-type contacts 220 may have a disk-shaped configuration as shown in FIG. 16A. For some applications, it may be desirable that one or more of the contacts be configured as a combination surface-type/penetrating-type contact 228, as depicted in FIG. 16B. In that event, insulating material 226 serves the dual purpose of electrically insulating a penetrating-contact portion 230 of the combination contact 228 from a surface-contact portion 232 of the combination contact 228 while also serving as a seal to prevent body fluid from leaking into the intraosseous housing mechanism 43. The combination contact 228 provides two contacts that can be used simultaneously and independently—the penetrating-contact portion 230 and the surface-contact portion 232—for sensing or control purposes; the depth to which portion 230 is allowed to penetrate into the brain may be adjusted according to the application and it may be gauged through disk portion 234 of the surface-contact portion 232.

For some applications, it may be desirable to place a structure 217 within the housing mechanism 41, such as a device containing an a sensor/stimulator array, incorporating a device positioning mechanism 240 that includes a support rod 241 that connects structure 217 to the device position system 240, as schematically represented in FIG. 16A, wherein the part 217 includes a plurality of sensors 216, as hereinbefore described. The structure 217 can be positioned in reference to the brain, including being moved in three dimensions and/or rotated by the device positioning mechanism 240, using electro-mechanical or other means, such as a system of gears that will be described herein for illustrative purposes. For example, support rod 241 can be connected at one end to a first track 244 that, for discussion purposes, is depicted as being disposed normal to the plane of FIG. 16A. The first track 244 utilizes a rack and pinion arrangement, or other suitable means, such that the movable structure 217 can be controllably displaced back and forth along the first track 244 by an electrically or mechanically driven x-axis driving mechanism 246. The first track 244 is in movable engagement with a second track 248 that for discussion purposes is depicted as being disposed in the plane of FIG. 16A and transversely to the first track 244. The first track 244 moves relative to the second track 248 using a rack and pinion arrangement, or other suitable means, such that the first track 244 can be controllably displaced back and forth along the second track 248 by an electrically or mechanically driven y-axis driving mechanism 250. Ends 252, 254 of the second track 248 are movably engaged to elevating mechanisms 256, 258 by rack and pinion arrangements, or other suitable means, such that the second track 248 can be controllably displaced along the elevating mechanisms 256, 258 by electrically or mechanically driven z-axis (radial) driving mechanisms 260, 262. For the particular size and functionality requirements of certain applications, one skilled in the art will appreciate that the rack and pinion arrangements mentioned herein may be replaced or augmented other systems of gears including bevel, worm, or sun-planet gears, hinges, pulley systems or hoists, and various hydraulic, magnetic, or other electro-mechanical systems for displacement used to transform linear to rotational motion and vice versa suitable for these purposes.

After the device positioning mechanism 240 is secured within housing mechanism 41 to provide a stable reference point, the x-axis driving mechanism 246 is activated to displace the structure 217 along the first track 244 to precisely place the movable structure 217 and thus, for example, contacts 216, along an x-axis relative to the brain 56 of the subject as indicated by the arrow designated by the numeral 263. The y-axis driving mechanism 250 is then activated to displace the first track 244 along the second track 248 to precisely locate the contacts 216 of the structure 217 along a y-axis relative to the brain 56 of the subject as indicated by the arrow designated by the numeral 264. It is to be understood that the manipulation of the x-axis driving mechanism 246 and/or the y-axis driving mechanism 250 may not be a single step but, instead, may be an iterative process in order to precisely locate the plurality of contacts 216 as desired relative to the brain 56 of the subject. FIGS. 16E-F provide top views illustrating the positioning of structure 217 as described above, while FIG. 16G provides a side view. One skilled in the art will appreciate that for some applications, such as when ease of access to compartments within structure 217 is a higher priority than unrestricted access to the entire brain surface below structure 217, it may be desirable to place structure 217 above, rather than below, these tracks 244, 248, while remaining in movable engagement as otherwise described herein. It is also to be understood that the invention may include an angular driving mechanism 265, such as a bevel gear arrangement or other suitable means, to controllably rotate the structure 217 in a horizontal plane relative to tracks 244, 248, as indicated by the arrow designated by numeral 268 in FIG. 16C. In such embodiments involving rotation of the structure 217, the shape of the structure 217 and of the intraosseous housing mechanism 43 is preferably a right circular cylinder. After the desired x-y location of the contacts has been established, the z-axis driving mechanisms 260, 262 are activated to displace the second track 248 along the elevating mechanisms 256, 258 to place the surface of structure 217 containing recording contacts 216 against the surface of the subject's brain 56 and can also be used to insert the penetrating contacts 218 into the tissue of the brain 56 of the subject as indicated by the arrow designated by numeral 270. In addition to the z-axis driving mechanism, the position of structure 217 may additionally be adjusted in manners not parallel to the x-y axes plane, for example in the direction of arrows 269 in FIG. 16D, by making use of a pivoting mechanism 267 that may include spring tension, electro-mechanical, or other means for positioning structure 217 so as to allow contacts 216 to make the desirable robust connections with underlying tissue. In another embodiment, the inner wall of the intraosseous housing mechanism 43, structure 217, or portions thereof, may be configured to conform to the shape of the brain when in close apposition to it.

Another embodiment of the present invention includes alternative means for positioning movable structure 217 in reference to underlying brain tissue, comprising placing structure 217 in movable engagement with a rotatable radial axis support 281 and attaching the edge of structure 217 to the radial wall of right circular cylindrically-shaped intraosseous housing mechanism 43 as illustrated in FIGS. 16H-I. FIG. 16H provides a top view and FIG. 16I provides a side angle view. The attachment can be made, for example, using a hook element 287 into a track 283 that travels around the perimeter of the radial wall of intraosseous housing mechanism 43. The hook element may be displaced along the track to position structure 217 via an electro-mechanical driving mechanism 285, or may passively slide around the track as radial axis support 281 rotates to position structure 217. More intricate placement of devices can be obtained using combinations of the types of movements described herein including, for example, the consideration of the entire visible contents of FIG. 16I as movable structure in and of itself that can be further displaced in the x, y, or z axes or rotated.

Another embodiment of the present invention includes means for ensuring that the intraosseous housing mechanism 43 can be attached to the skull in a manner that ensures that the inner surface 108 of its inner wall 106 can be located in a desirable position relative to the underlying tissue, such as positioned to be flush with the inner surface 110 of the skull 47. This can be achieved by affixing mounting brackets 271, which may be endowed with tracks, to the skull 47 at the margin of cavity 45 and then attaching housing mechanism 41 to these mounting brackets in a manner configured to allow the desired displacement in the radial axis as indicated by numeral 270 in FIG. 16A. Such displacement means may include, for example, the use of rollers 275 on tracks 271 or a threaded connection between housing mechanism 41 and the mounting brackets which enables housing mechanism 41 to be screwed into place.

Figure 17A:
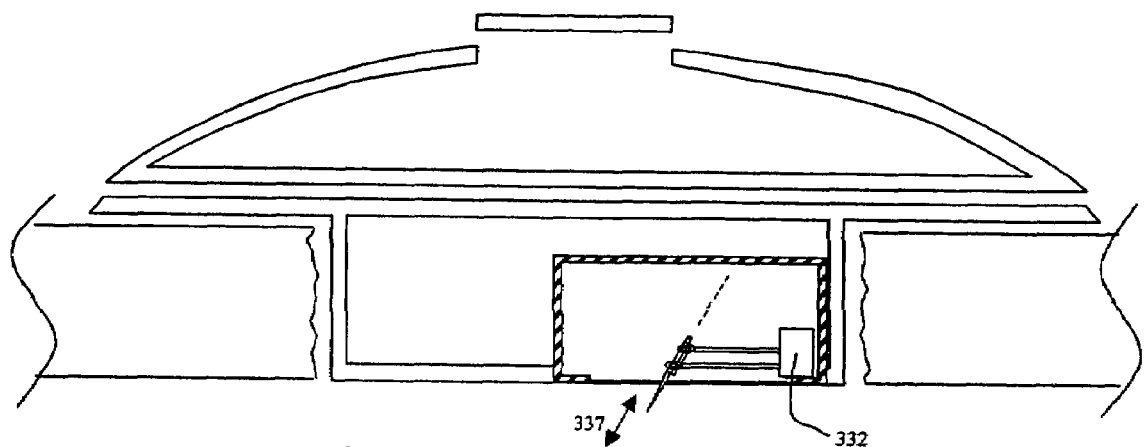
FIG. 17 is a schematic cross-sectional view of an embodiment of the cerebral interface system that includes a device positioning mechanism and an extendible/retractable telescoping probe as an example device to be positioned into the brain thereby, according to the present invention.
Figure 17B:
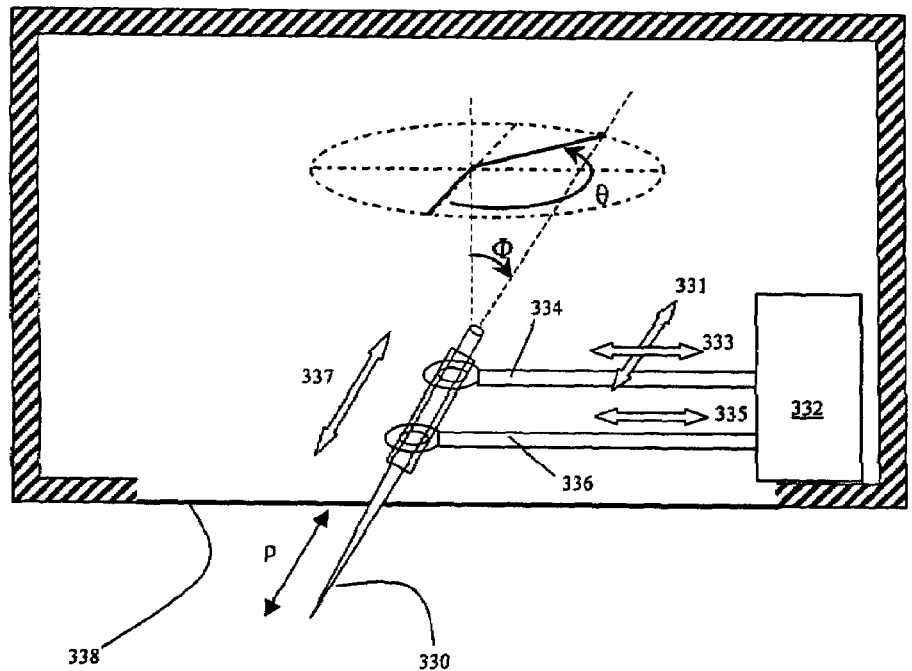

In another embodiment of the invention, the housing mechanism includes an internal positioning mechanism used to control positioning of devices or other elements housed within the housing mechanism. FIG. 17 provides a schematic illustration of an embodiment of the invention in which an extendable/retractable probe 330, such as a biopsy needle or electrode/sensor, is positioned by positioning mechanism 332 relative to the skull or brain structures in a manner that allows the probe to reach a particular target or targets upon deployment. In this illustration, movable arms 334, 336 are displaced in the plane parallel to the inner wall 106 of the intraosseous housing mechanism 43 as indicated by arrows 331, 333, and 335, in order to control the angles made by the position of the probe as measured relative to the radial axis of the intraosseous housing mechanism 43 and indicated by $\theta$ and $\phi$ in FIG. 17B. Upon achieving the desired position angles, the probe may be extended a desired distance, indicated by p, along its own axis, as indicated by arrow 337 to extend through resealable membrane 338 to reach the target tissue. One skilled in the art will appreciate that micro-electromechanical machining (MEMS) technology may be utilized to attain the described functionality of the various positioning mechanisms described herein.

It will be appreciated that the sensing devices described above may also be used as part of one or more output mechanisms, providing output to the brain or other organs, for example:

(a) the sensing devices hereinbefore described can be used to deliver an electric current to specific regions of the brain 56, (b) the inner wall 106 of the intraosseous housing mechanism 43 may be structured and configured to cool or warm surrounding tissue, and (c) the housing mechanism 41 may contain drug delivery reservoirs and pumping mechanisms to distribute substances to the brain 56 and/or other portions of the body.

Figure 18A:
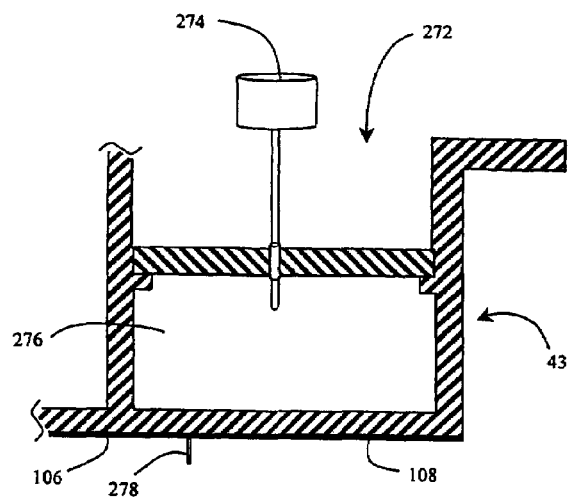
FIG. 18 are schematic cross-sectional views of an embodiment of the cerebral interface system that includes a treatment portion for multimodal therapy delivery, including thermal regulation, according to the present invention.
Figure 18B:
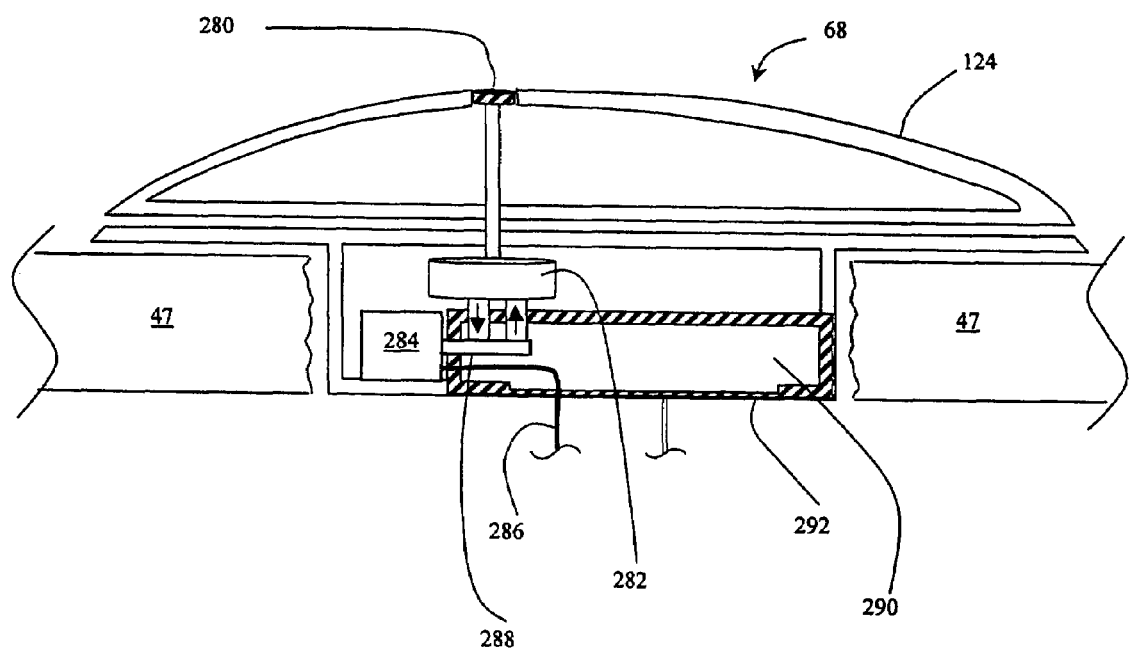

More specifically, the housing mechanism 41 may include a treatment portion 272 spaced adjacently to all or a portion of the inner wall 106 of the intraosseous housing mechanism 43 as schematically depicted in FIG. 18. For treatments requiring heating or cooling of surrounding tissue, an external source 274 may be connected in communication with an interior cavity 276 of the treatment portion 272 to heat or cool the thermally conductive inner wall 106 of the intraosseous housing mechanism 43 to thereby transfer thermal energy to, or remove thermal energy from, the tissue in abutting engagement with the inner surface 108 of the inner wall 106.

For some such applications, it may be desirable to provide one or more thermally conductive probes 278 in thermal communication with, and extending outwardly from, the conductive inner wall 106 to thereby heat or cool, as appropriate, tissue at or below the surface. Those skilled in the art can appreciate that transferring thermal energy to, or exchanging thermal energy with, intracranial tissues may take place through tubes or probes whose length depends on the required application. Details of how this may be accomplished, subject only to appropriate modifications for incorporation within the subject cerebral interface system, are provided in U.S. Pat. No. 6,793,670, issued Sep. 21, 2004 and entitled "Multi-Modal System for Detection and Control of Changes in Brain State," which is incorporated by reference. Appropriate insulation is provided between the thermally active and inactive elements of the intraosseous housing mechanism 43 and between the intraosseous housing mechanism 43 and the bone and scalp. FIG. 18A illustrates a schematic side view of an exemplary treatment portion 272 containing a reservoir access 280 that is in communication with a reservoir 282. A control mechanism 284 comprising, for example, a microprocessor for receiving signals from the communication mechanism 63 including, in this case, from one or more temperature sensors 286 placed on the surface of, or within, the brain 56 and utilizing a bidirectional pump/temperature regulator 288 to control the coolant level within chamber 290 to thereby control the temperature of the adjacent brain tissue through a thermally conductive inner surface 292 of the treatment portion 272 and/or one or more thermally conductive probes 278. One skilled in the art will appreciate that the cooling described herein may alternatively be achieved via electrical means using, for example, a Peltier junction mechanism.

Figure 19:
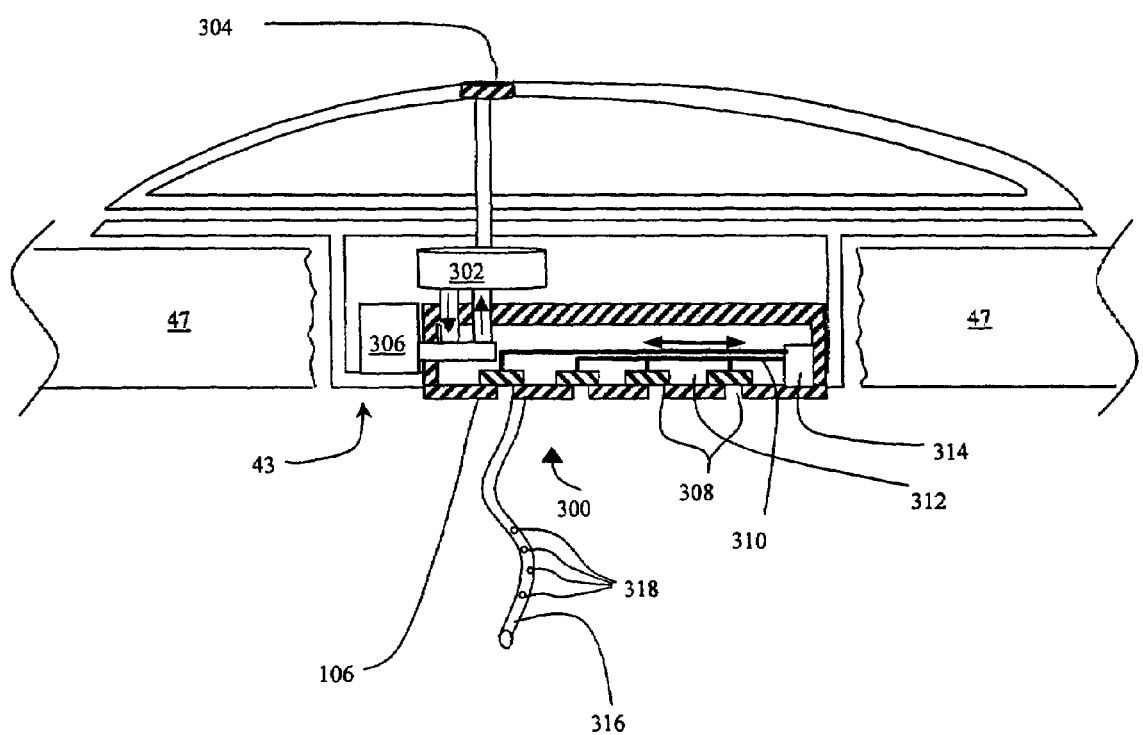
FIG. 19 is a schematic cross-sectional view of an embodiment of the cerebral interface system that includes a substance delivery/collection portion having a shutter mechanism, according to the present invention.

Alternately or in addition to the aforesaid treatment portion 272, it may be desirable that the intraosseous housing mechanism 43 include a medicament portion 300, as schematically depicted in FIG. 19. This treatment portion 300 may be used to administer a medicament or substance to the brain 56 or other organ. The substance or substances may be placed in at least one reservoir 302 through an externally accessible access 304, and its delivery may be controlled by a control mechanism 306 that may include a uni-directional or bi-directional pump/pressure regulator and a microprocessor. In one embodiment, one or more throughbores or pores 308 extend through a portion of the inner wall 106 of the intraosseous housing mechanism 43 that is encompassed by the medicament portion 300. A shutter mechanism 310 having openings 312, that can be selectively mated with the pores 308, is slidably mounted on the inside surface of the inner wall 106 that is inside the intraosseous housing mechanism 43. An electrically driven shutter-operating mechanism 314, which may be controlled by control mechanism 306, is structured and configured to operatively displace the shutter mechanism 310 to and from an "open" configuration wherein the openings 312 are aligned with the pores 308 and a "closed" configuration wherein the openings 312 are not aligned with the pores 308. In the "open" configuration, medicament contained within the medicament portion 300 can controllably and selectively leak into the tissue adjacent to the pores 308 for treatment purposes and the like. If desired, a small positive pressure, such as with a micropump may be applied to the interior of the medicament portion 300 to assist with administering the medicament through the pores 308. In the "closed" configuration, mismatching of the openings 312 with the pores 308 causes a fluid-tight seal to be established between the shutter operating mechanism 314 and the inside surface of the inner wall 106 of the intraosseous housing mechanism 43 to thereby prevent the medicament contained in the medicament portion 300 from leaking onto the adjacent tissue.

In an alternative or complementary embodiment, passively, by capillary action, by gravity or by a slight negative pressure, fluid samples may be collected from the tissue adjacent to the pores 308, which may be stored within reservoir 302 or in a separate reservoir configured for this purpose, and removed through a reservoir access 304. Moreover, in either of the above illustrative examples, one skilled in the art will appreciate that a similar control mechanism may be used in conjunction with catheters/tubes 316 in place of, or in addition to, the described pores 308 and shutter mechanism 310 to transfer medicament/collect fluid. These catheters/tubes may have one or more holes 318 to increase surface delivery area.

Other types of devices that may be included as an integral part of the housing mechanism 41 of the present invention include a clock and/or global positioning system (GPS) device. Information from such devices may be used, for example, to log events detected by other monitoring or control devices within the associated apparatus, or for use in providing an automated warning to emergency medical staff with physical location of the subject and precise time/duration of a detected predetermined event.

It is to be understood that the type of application of the present invention is limited only by the type of sensors and devices available for use with various elements of the invention as described herein. In other words, the present invention can be used for remote sensing, analysis, monitoring, recording, detection, prediction, warning, control, prevention and/or treatment or control of various changes of state of the brain and/or body organs.

Further, the housing mechanism 41 may be configured with a boundary between a sterile zone 211 thereof and a non-sterile zone 210 thereof wherein the communication link 71 provides means for communicating between devices on either side of such boundary. This allows the user to easily access, modify, or replace various devices from the non-sterile zone without risk of infection to the subject. These may include, for example, batteries, data storage devices, or fluid samples. In one embodiment, the interior of intraosseous housing mechanism 43 may serve as a sterile chamber and the interior of the auxiliary housing mechanism 68 may serve as the non-sterile chamber, with hermetically sealed ports 238 between various chambers utilized as part of communication link 71, which remain functional during displacement of auxiliary housing mechanism 68 with respect to intraosseous housing mechanism 43. Sample displacement direction is indicated by numeral 239 in FIG. 15A.

One skilled in the art will also appreciate that the sensors that obtain signals representative of brain or body state of the subject may also be located outside of the brain 56, possibly inside the housing mechanism 41 itself (e.g., an accelerometer), elsewhere in the subject's body (e.g., a heart monitor), or may even be external and attached to (e.g., a scalp electrode) or separate from the subject's body (e.g., an infrared motion sensor, video or audio recordings, or thermographic images).

Other types of devices that may be housed within the cerebral interface system include lasers that may be directed at tissue for spectroscopic and/or tissue ablation purposes (including short-pulse lasers capable of progressively ablating very small amounts of tissue in a columnar manner radially inward from the tip of the laser), one or more radio-frequency ablation mechanisms, needle biopsy mechanisms, and elements that may be used for neurosurgical guidance in implanting sensors or other elements within the brain 56 for use in conjunction with housing mechanisms 43. Such elements may include stable fiducial markers placed at one or more locations within the housing mechanism or on its outer surface 120.

It is to be understood that although various functions that may be performed by devices within the housing mechanism are described herein as mechanisms identified by a name corresponding to the particular function, it is to be understood that any device or devices within the cerebral interface system may be configured to perform one or more of the described functions. Moreover, while the identified functions may be performed jointly or separately within one or more devices within the cerebral interface system, multiple devices may perform the same function, providing a degree of redundancy and robustness. Further, the entire cerebral interface system can be made fully integrated so that any and all functions can occur seamlessly without designated hardware.

It is also to be understood that while certain forms of the present invention have been illustrated and described herein, it is not to be limited to the specific forms or arrangement of parts described and shown.

What is claimed and desired to be secured by Letters Patent is as follows:

1. An organ interface system for communicatively connecting at least one organ of a body with a user, comprising:
   (a) at least one housing mechanism including an intraosseous portion and an extraosseous auxiliary portion, the at least one housing mechanism configured to be spaced at least in part within a bone of a subject and having at least one device contained or partially contained therein;
   (b) attaching means configured to attach the at least one housing mechanism to the bone, the attaching means being slidable for repositioning of the auxiliary housing mechanism in reference to the intraosseous housing mechanism to allow access to the intraosseous housing mechanism without removing the auxiliary housing mechanism; and
   (c) at least one communication mechanism configured to communicatively connect the at least one organ to the at least one device; and
   (d) wherein the at least one device is configured to operatively sense, monitor, store, record, log, transmit, analyze, quantify, detect changes in, predict changes in, warn of changes in, modify, or control the state or activity in the at least one organ.

2. An organ interface system for communicatively connecting at least one organ of a body with a user, comprising:
   (a) at least one housing mechanism configured to be spaced at least in part within a bone of a subject, the at least one housing mechanism having at least one device contained or partially contained therein;
   (b) attaching means configured to attach the at least one housing mechanism to the bone;
   (c) at least one communication mechanism configured to communicatively connect the at least one organ to the at least one device; and
   (d) at least one movable structure that is in moveable engagement with a device positioning mechanism having:
      (1) a first track with a first mounting mechanism structured to connect the at least one movable structure to the first track,
      (2) a second track with a second mounting mechanism structured to mount the first track thereon, the second track having first and second ends,
      (3) elevation mechanisms with third mounting mechanisms structured to mount the first and second ends of the second track to the elevation mechanisms,
      (4) an x-axis driving mechanism structured to controllably and operatively displace the housing mechanism along the first track,
      (5) a y-axis driving mechanism structured to controllably and operatively displace the first track along the second track, and
      (6) z-axis driving mechanisms structured to controllably and operatively displace the first and second ends of the second track along the elevation mechanisms, and
   (e) wherein the at least one device is configured to operatively sense, monitor, store, record, log, transmit, analyze, quantify, detect changes in, predict changes in, warn of changes in, modify, or control the state or activity in the at least one organ.

3. The system as described in claim 2, wherein the first mounting mechanism includes an angular driving mechanism configured to rotate the at least one movable structure about an axis of rotation.

* * * * *